United States Patent
Loose et al.

(10) Patent No.: US 11,617,745 B2
(45) Date of Patent: Apr. 4, 2023

(54) COMPOSITIONS AND METHODS FOR GENERATING HAIR CELLS BY DOWNREGULATING FOXO

(71) Applicant: Frequency Therapeutics, Inc., Woburn, MA (US)

(72) Inventors: Christopher Loose, Winchester, MA (US); Will McLean, North Haven, CT (US); Megan Harrison, Middletown, CT (US); Melissa Hill-Drzewi, Durham, CT (US)

(73) Assignee: Frequency Therapeutics, Inc., Lexington, MA (US)

( * ) Notice: Subject to any disclaimer, the term of this patent is extended or adjusted under 35 U.S.C. 154(b) by 0 days.

(21) Appl. No.: 16/544,795

(22) Filed: Aug. 19, 2019

(65) Prior Publication Data

US 2020/0078350 A1 Mar. 12, 2020

Related U.S. Application Data

(60) Provisional application No. 62/719,273, filed on Aug. 17, 2018.

(51) Int. Cl.
| | | |
|---|---|---|
| *A61K 31/47* | (2006.01) | |
| *A61K 31/19* | (2006.01) | |
| *A61K 9/00* | (2006.01) | |
| *A61K 47/34* | (2017.01) | |
| *A61P 27/16* | (2006.01) | |
| *A61K 9/06* | (2006.01) | |

(52) U.S. Cl.
CPC ............ *A61K 31/47* (2013.01); *A61K 9/0046* (2013.01); *A61K 9/0053* (2013.01); *A61K 9/06* (2013.01); *A61K 31/19* (2013.01); *A61K 47/34* (2013.01); *A61P 27/16* (2018.01)

(58) Field of Classification Search
CPC .... A61K 31/19; A61K 31/4375; A61K 31/47; A61K 9/0019; A61K 9/0046; A61K 9/06; A61K 9/08; A61K 9/0053; A61K 9/122; A61K 47/10; A61K 47/34; A61K 45/06; C12N 5/062; C12N 2501/60; A61P 27/16
See application file for complete search history.

(56) References Cited

U.S. PATENT DOCUMENTS

| | | |
|---|---|---|
| 5,059,591 A | 10/1991 | Janoff et al. |
| 5,421,818 A | 6/1995 | Arenberg |
| 5,474,529 A | 12/1995 | Arenberg |
| 5,476,446 A | 12/1995 | Arenberg |
| 5,731,144 A | 3/1998 | Toothman et al. |
| 5,731,424 A | 3/1998 | Toothman et al. |
| 5,837,681 A | 11/1998 | Magal |
| 6,045,528 A | 4/2000 | Arenberg et al. |
| 6,124,449 A | 6/2000 | Gold et al. |
| 6,090,383 A | 7/2000 | Dasch et al. |
| 6,177,434 B1 | 1/2001 | Kopke et al. |
| 6,194,466 B1 * | 2/2001 | Cottingham ......... A61K 31/155 514/635 |
| 6,419,928 B1 | 7/2002 | Dasch et al. |
| 6,476,031 B1 | 11/2002 | Chakravarty et al. |
| 6,509,318 B1 | 1/2003 | Bhatnagar et al. |
| 6,593,290 B1 | 7/2003 | Gao |
| 6,943,191 B1 | 9/2005 | Narayanan et al. |
| 7,030,125 B2 | 4/2006 | Munchhof et al. |
| 7,087,626 B2 | 8/2006 | Beight et al. |
| 7,151,169 B2 | 12/2006 | Thompson et al. |
| 7,223,766 B2 | 5/2007 | Dugar et al. |
| 7,387,614 B2 | 6/2008 | Staecker |
| 7,498,031 B2 | 3/2009 | Fujioka et al. |
| 7,514,445 B2 | 4/2009 | Freyne et al. |
| 7,723,486 B2 | 5/2010 | Ledbetter et al. |
| 8,071,591 B2 | 12/2011 | Nomura et al. |
| 8,207,216 B2 | 6/2012 | Kozikowski et al. |
| 8,298,825 B1 | 10/2012 | Hochedlinger et al. |
| 8,377,886 B2 | 2/2013 | Susztak et al. |
| 8,575,122 B2 | 11/2013 | Lichter et al. |
| 8,686,042 B2 | 4/2014 | Gil et al. |
| 8,709,385 B2 | 4/2014 | Tamarkin et al. |
| 8,771,754 B2 | 7/2014 | Hallahan |
| 8,784,870 B2 | 7/2014 | Lichter et al. |
| 8,852,626 B2 | 10/2014 | Lichter et al. |
| 9,333,171 B2 | 5/2016 | Lichter et al. |
| 9,347,042 B2 | 5/2016 | Shimmura et al. |
| 10,041,046 B2 | 8/2018 | Karp et al. |
| 10,041,047 B2 | 8/2018 | Karp et al. |
| 10,568,883 B2 | 2/2020 | Karp et al. |
| 10,954,490 B2 | 3/2021 | Karp et al. |
| 11,021,687 B2 | 6/2021 | Karp et al. |

(Continued)

FOREIGN PATENT DOCUMENTS

| | | |
|---|---|---|
| CA | 2268331 | 5/1998 |
| CA | 2984541 | 11/2007 |

(Continued)

OTHER PUBLICATIONS

Nagashima et. al., Molecular Pharmacology, 2010, The Amer. Soc. Pharm. & Exp. Ther., vol. 78(5), pp. 961-970 (Year: 2010).*

Tate, Principles of Hearing Aid Audiology, 1994, Chapter 2, pp. 20-40 (Year: 1994).*

Ahn et al. (2014). "GSK3?, but not GSK3?, inhibits the neuronal differentiation of neural progenitor cells as a downstream target of mammalian target of rapamycin complex1." Stem cells and development. 23(10): 1121-33.

Alford et al. (2014). "American College of Medical Genetics and Genomics Guideline for the Clinical Evaluation and Etiologic Diagnosis of Hearing Loss." Genetics in Medicine: Official Journal of the American College of Medical Genetics. vol. 16, pp. 347-355.

(Continued)

*Primary Examiner* — Sarah Pihonak
(74) *Attorney, Agent, or Firm* — Cooley LLP; Cynthia A. Kozakiewicz; Andrew Henderson

(57) ABSTRACT

Provided are compositions and methods comprising a FOXO inhibitor for increasing proliferation of Lgr5+ cochlear cells, and related methods of treating hearing loss.

15 Claims, 3 Drawing Sheets

(56) References Cited

U.S. PATENT DOCUMENTS

| | | |
|---|---|---|
| 11,162,071 B2 | 11/2021 | Loose et al. |
| 2003/0028905 A1 | 2/2003 | Knaus et al. |
| 2004/0006030 A1 | 1/2004 | Monia et al. |
| 2004/0015781 A1 | 1/2004 | Brown et al. |
| 2004/0038856 A1 | 2/2004 | Chakravarty et al. |
| 2004/0138188 A1 | 7/2004 | Higgins et al. |
| 2004/0147574 A1 | 7/2004 | Munchhof |
| 2004/0204431 A1 | 10/2004 | Scarborough et al. |
| 2005/0032835 A1 | 2/2005 | Pandey et al. |
| 2005/0227936 A1 | 10/2005 | McSwiggen et al. |
| 2005/0245508 A1 | 11/2005 | Weller et al. |
| 2005/0245520 A1 | 11/2005 | Dodie et al. |
| 2005/0287127 A1 | 12/2005 | Li et al. |
| 2005/0287128 A1 | 12/2005 | Guerciolini et al. |
| 2006/0003929 A1 | 1/2006 | Bier et al. |
| 2006/0229266 A1 | 10/2006 | Kumar et al. |
| 2007/0066632 A1 | 3/2007 | Hart et al. |
| 2007/0088080 A1 | 4/2007 | Gordillo et al. |
| 2007/0155722 A1 | 7/2007 | Li et al. |
| 2007/0167918 A1 | 7/2007 | Reed et al. |
| 2008/0015161 A1 | 1/2008 | Vornlocher et al. |
| 2008/0108656 A1 | 5/2008 | Pandey et al. |
| 2008/0275030 A1* | 11/2008 | Gizurarson .......... A61K 9/0043 514/220 |
| 2009/0036382 A1 | 2/2009 | Bressan et al. |
| 2009/0270497 A1 | 10/2009 | Buggy |
| 2009/0305333 A1 | 12/2009 | He et al. |
| 2009/0325938 A1 | 12/2009 | Lichter et al. |
| 2010/0267141 A1 | 10/2010 | Shi |
| 2010/0292205 A1 | 11/2010 | Lefker et al. |
| 2011/0135756 A1 | 6/2011 | Owens et al. |
| 2011/0166060 A1 | 7/2011 | Simons et al. |
| 2011/0305674 A1 | 12/2011 | Edge et al. |
| 2012/0059021 A1 | 3/2012 | Biechele |
| 2012/0196312 A1 | 8/2012 | Sato et al. |
| 2012/0277199 A1 | 11/2012 | Ye et al. |
| 2013/0079329 A1 | 3/2013 | Hood |
| 2013/0189327 A1 | 7/2013 | Ortega et al. |
| 2013/0324594 A1 | 12/2013 | Guthrie |
| 2014/0004556 A1 | 1/2014 | Heller et al. |
| 2014/0023615 A1* | 1/2014 | Hsu .................. A61K 47/22 424/85.2 |
| 2014/0243227 A1 | 8/2014 | Clevers et al. |
| 2014/0248696 A1 | 9/2014 | Zhang et al. |
| 2015/0025096 A1 | 1/2015 | Thies et al. |
| 2015/0240212 A1 | 8/2015 | Peterson et al. |
| 2015/0250747 A1* | 9/2015 | Bumpus .................. A61K 31/19 514/557 |
| 2015/0320877 A1 | 11/2015 | Messersmith et al. |
| 2015/0329821 A1 | 11/2015 | Ang et al. |
| 2016/0032240 A1 | 2/2016 | Heller et al. |
| 2016/0194604 A1 | 7/2016 | Karp et al. |
| 2017/0000728 A1 | 1/2017 | Lichter et al. |
| 2017/0071937 A1 | 3/2017 | Karp et al. |
| 2017/0226477 A1 | 8/2017 | Karp et al. |
| 2017/0252449 A1 | 9/2017 | Loose et al. |
| 2017/0349884 A1 | 12/2017 | Karp et al. |
| 2018/0214458 A1 | 8/2018 | Loose et al. |
| 2019/0017015 A1 | 1/2019 | Karp et al. |
| 2019/0060371 A1 | 2/2019 | McLean |
| 2019/0093079 A1 | 3/2019 | Loose et al. |
| 2019/0350845 A1 | 11/2019 | Lichter et al. |
| 2020/0080054 A1 | 3/2020 | Loose et al. |
| 2020/0080055 A1 | 3/2020 | Loose et al. |
| 2020/0323853 A1 | 10/2020 | Karp et al. |
| 2021/0301254 A1 | 9/2021 | Karp et al. |
| 2021/0363491 A1 | 11/2021 | Karp et al. |

FOREIGN PATENT DOCUMENTS

| | | |
|---|---|---|
| CN | 1319968 | 6/2007 |
| CN | 101341138 | 11/2012 |
| CN | 103361300 | 10/2013 |
| CN | 104726395 | 6/2015 |
| CN | 104894060 | 9/2015 |
| CN | 105853421 | 8/2016 |
| CN | 107073042 | 8/2017 |
| CN | 108291197 | 7/2018 |
| EP | 0945464 | 9/1999 |
| EP | 1739087 | 1/2007 |
| EP | 1961748 | 8/2008 |
| EP | 2636731 | 9/2013 |
| EP | 2765188 | 8/2014 |
| EP | 2963108 | 1/2016 |
| EP | 3277801 | 10/2020 |
| JP | 2012148995 | 8/2012 |
| WO | WO-1996/027610 | 9/1996 |
| WO | WO-1996/040094 | 12/1996 |
| WO | WO-1998/019700 | 5/1998 |
| WO | WO-1999/058128 | 11/1999 |
| WO | WO-2000/012497 | 3/2000 |
| WO | WO-2000/031135 | 6/2000 |
| WO | WO-2000/059939 | 10/2000 |
| WO | WO-2001/085685 | 11/2001 |
| WO | WO-2002/094833 | 11/2002 |
| WO | WO-2003/037891 | 5/2003 |
| WO | WO-2003/097639 | 11/2003 |
| WO | WO-2004/013135 | 2/2004 |
| WO | WO-2004/021989 | 3/2004 |
| WO | WO-2004/026307 | 4/2004 |
| WO | WO-2004/026865 | 4/2004 |
| WO | WO-2004/026871 | 4/2004 |
| WO | WO-2004/067530 | 8/2004 |
| WO | WO-2005/009939 | 2/2005 |
| WO | WO-2005/039570 | 5/2005 |
| WO | WO-2005/097119 | 10/2005 |
| WO | WO-2006/018633 | 2/2006 |
| WO | WO-2006/018967 | 2/2006 |
| WO | WO-2006/100490 | 9/2006 |
| WO | WO-2007/018818 | 2/2007 |
| WO | WO-2007/047509 | 4/2007 |
| WO | WO-2007/048857 | 5/2007 |
| WO | WO-2007/102770 | 9/2007 |
| WO | WO-2008/010852 | 1/2008 |
| WO | WO-2008/076556 | 6/2008 |
| WO | WO-2008/077138 | 6/2008 |
| WO | WO-2009/017453 | 2/2009 |
| WO | WO-2009/017455 | 2/2009 |
| WO | WO-2009/032667 | 3/2009 |
| WO | WO-2009/132050 | 10/2009 |
| WO | WO-2010/060088 | 5/2010 |
| WO | WO-2010/068955 | 6/2010 |
| WO | WO-2010/075551 | 7/2010 |
| WO | WO-2010/090513 | 8/2010 |
| WO | WO-2010/104205 | 9/2010 |
| WO | WO-2011/019957 | 2/2011 |
| WO | WO-2011/050476 | 5/2011 |
| WO | WO-2011/079841 | 7/2011 |
| WO | WO-2011/089416 | 7/2011 |
| WO | WO-2011/116930 | 9/2011 |
| WO | WO-2011/123572 | 10/2011 |
| WO | WO-2011/143511 | 11/2011 |
| WO | WO-2012/018933 | 2/2012 |
| WO | WO-2012/024404 | 2/2012 |
| WO | WO-2012/103012 | 8/2012 |
| WO | WO-2012/141471 | 10/2012 |
| WO | WO-2013/051722 | 4/2013 |
| WO | WO-2013/124413 | 8/2013 |
| WO | WO-2014/003098 | 1/2014 |
| WO | WO-2014/013255 | 1/2014 |
| WO | WO-2014/039908 | 3/2014 |
| WO | WO-2014/050779 | 4/2014 |
| WO | WO-2014/059383 | 4/2014 |
| WO | WO-2014/083132 | 6/2014 |
| WO | WO-2014/159356 | 10/2014 |
| WO | WO-2015/038704 A1 | 3/2015 |
| WO | WO-2015/168149 | 11/2015 |
| WO | WO-2015/175783 | 11/2015 |
| WO | WO-2016/029021 | 2/2016 |
| WO | WO-2016/037016 | 3/2016 |
| WO | WO-2017/048193 | 3/2017 |
| WO | WO-2017/120543 | 7/2017 |
| WO | WO-2017/132530 | 8/2017 |

(56) References Cited

FOREIGN PATENT DOCUMENTS

| WO | WO-2017/151907 | 9/2017 |
|---|---|---|
| WO | WO-2018/125746 | 7/2018 |
| WO | WO-2019/183572 | 9/2019 |
| WO | WO-2020/037323 | 2/2020 |
| WO | WO-2020/037325 | 2/2020 |
| WO | WO-2020/037326 | 2/2020 |
| WO | WO-2020/163812 | 8/2020 |
| WO | WO-2020/163813 | 8/2020 |
| WO | WO-2020/163814 | 8/2020 |

OTHER PUBLICATIONS

Almeida et al. (2014). "In Situ Gelling Systems: A Strategy to Improve the Bioavailability of Ophthalmic Pharmaceutical Formulations." Drug Discov. Today, 19(4): 400-12.
Arnold et al. (2011). "Zinc for Attention-Deficit/Hyperactivity Disorder: Placebo-Controlled Double-Blind Pilot Trial Alone and Combined with Amphetamine." Journal of Child and Adolescent Psychopharmacology, vol. 21(1): 1-19.
Associacao Brasileira de Otorrinolaringologia e Cirurgia Cervicofacial et al. (2012). "Sensorineural Hearing Loss: Radiologic Diagnosis." Revista da Associacao Medica Brasileira, vol. 58, pp. 519-529.
Barker et al. (2007). "Identification of stem cells in small intestines and colon by marker gene Lgr5." Nature Publishing Group. vol. 449, No. 25 1003-7.
Barker et al. (2010). "Lgr5-'-ve stem cells drive self-renewal in the stomach and build long-lived gastric units in vitro." Cell Stem Cell. vol. 6, 25-36.
Bermingham et al. (1999). "Math 1: An Essential Gene for the Generation of Inner Ear Hair Cells." Science, 284: 1837-1841.
Bohl et al. (2012). "Development of a Specially Tailored Local Drug Delivery System for the Prevention of Fibrosis After Insertion of Cochlear Implants Into the Inner Ear." Journal of Materials ScienceMaterials in Medicine, vol. 23:2151-2162.
Borenstein, J.T. (2011). "Intracochlear Drug Delivery Systems." Expert Opinion on Drug Delivery, vol. 8, No. 9, pp. 1161-1174.
Bramhall et al. (2014). "Lgr5-Positive Supporting Cells Generate New Hair Cells in the Postnatal Cochlea." Stem Cell Reports. 2(3): 311-322.
Brigande et al. (2009). "Quo vadis, hair cell regeneration?" Nat. Neurosci., 12(6): 679-685.
Bryan. (2011). "Presenting The 2011 DRF Grantees. Hearing Health: A Publication of Deafness Research Foundation." p. 42-50, Retrieved from the Internet: URL:http://hearinghealthfoundation.org/lib/sitefiles/pdf/HH_Fall2011_Grantees_REV.11.11.11.pdf.
Buczacki et al. (2013). "Intestinal label-retaining cells are secretory precursors expressing Lgr5," Nature, 495: 65-72.
Butler et al. (2010). "Rational Design and Simple Chemistry Yield a Superior, Neuroprotective HDAC Inhibitor, Tubastatin A," J. Am. Chem. Soc., vol. 132: 10842-10846.
Byfield et al. (2004). "Lateral Signaling Enhances TGF-J3 Response Complexity." Trends Cell Biol., 14(3): 107-111.
Byfield et al. (2004). "SB-505124 is a Selective Inhibitor of Transforming Growth Factor-J3 Type I Receptors ALK4, ALK5, and ALK7." Molecular Pharmacology. vol. 65, No. 3, pp. 744-752.
Callahan et al. (2002). "Identification of Novel Inhibitors of the Transforming Growth Factor Betal (TGF-betal) Type 1 Receptor (ALK5)." J. Med. Chem., vol. 45., No. 5, pp. 999-1001.
Causey et al. (1984). "The Maryland CNC Test: normative studies." Audiology 23(6): 552-568.
Chai et al. (2011). "Dynamic Expression of Lgr5, a Wnt Target Gene, in the Developing and Mature Mouse Cochlea." J. Assoc. Res. Otolaryngology. 12(4): 455-469.
Chai et al. (2012). "Wnt signaling induces proliferation of sensory precursors in the postnatal mouse cochlea." Proc. Nat'l. Acad. Sci. USA. 109(21): 8167-8172.
Chen et al. (2005). ""Inner Ear Drug Delivery Via a Reciprocating Perfusion System in the Guinea Pig,"" Journal of Controlled Release : Official Journal of the Controlled Release Society, 110: 1-9.
Chen et al. (2007) "Preliminary Study on Brain-Targeted Drug Delivery Via Inner Ear," Actapharmaceutica Sinica, 42(10):1102-1106.
Chen et al. (2009). "Aminoglycoside-induced histone deacetylation and hair cell death in the mouse cochlea," J. Neurochem., 108(5): 1226-1236.
Cox et al. (2014). "Spontaneous Hair Cell Regeneration in the Neonatal Mouse Cochlea in Vivo." Development. vol. 141, No. 4, pp. 816-829.
Crosnier et al. (2006). "Organizing cell renewal in the intestine: stem cells, signals and combinatorial control." Nature Reviews Genetics, 7: 349-359.
Dai et al. (2002). "Human Serum and Glucocorticoid-Inducible Kinase-Like Kinase (SGKL) Phosphorylates Glycogen Syntheses Kinase 3 Beta (GSK-3beta) at Serine-9 Through Direct Interation." Biolchem. Biophys. Res. Commun., vol. 293, No. 4, pp. 1191-1196.
Database accession No. NLM25167568. Yeap Li-Ling et al. (2014). "Valproate-induced reversible sensorineural hearing loss: a case report with serial audiometry and pharmacokinetic modelling during a valproate rechallenge." Epileptic Disorders : International Epilepsy Journal With Videotape Sep. 2014, vol. 16, No. 3, Sep. 2014 (Sep. 2014), pp. 375-379, ISSN: 1294-9361.
Database accession No. PREV199191056930. Armon C. et al. (1990). "Sensorineural Hearing Loss a Reversible Effect of Valproic Acid." vol. 40, No. 12 pp. 1896-1898, ISSN: 0028-3878.
Database accession No. PREV201600270745. Benajiba Lina et al. (2015). "Identification of a First in Class GSK3-Alpha Selective Inhibitor as a New Differentiation Therapy for AML." Blood,vol. 126, No. 23. ISSN: 0006-4971 (print).
Davies et al. (2001). "The Interaction Between J3-Catenin, GSK3J3 and APC After Motogen Induced Cell-Cell Dissociation, and Their Involvement in Signal Transduction Pathways in Prostate Cancer." International Journal of Oncology. vol. 18, No. 4, pp. 843-847.
Davis et al. (2008). "Mesodermal Fate Decisions of a Stem Cell: the Wnt Switch," Cell Mol Life Sci., 65(17):2658-74. (abstract only).
De Los Angeles et al. (2013). "A chemical logic for reprogramming to pluripotency," Cell Research, vol. 23, No. 12, pp. 1337-1338.
Doble et al. (2007). "Functional redundancy of GSK-3alpha and GSK-3beta in Wnt/beta-catenin signaling shown by using an allelic series of embryonic stem cell lines." Developmental Cell, vol. 12, No. 6, p. 957-971.
Drottar et al. (2006). "The Histone Deacetylase Inhibitor Sodium Butyrate Protects Against Cisplatin-Induced Hearing Loss in Guinea Pigs," Laryngoscope, 116(2): 292-296.
Dumont et al. (2003). "Targeting the TGFJ3 Signaling Network in Hun1an Neoplasia." Cancer Cell. vol. 3, No. 6, pp. 531-536.
Engleder et al. (2014). "Preclinical Evaluation of Thermo reversible Triamcinolone Acetonide Hydrogels for Drug Delivery to the Inner Ear." International Journal of Pharmaceutics. vol. 471, No. 1-2, pp. 297-302.
Espinoza et al. (2003). "Phosphorylation by Glycogen Synthase Kinase-3J3 Down-Regulates Notch Activity, a Link for Notch and Wnt Pathways." Journal of Biological Chemistry. vol. 278, No. 34, pp. 32227-32235.
Farin et al. (2012). "Redundant sources of Wnt regulate intestinal stem cells and promote formation ofPaneth cells," Gastroenterology, 143: 1518-1529.
Foltz et al. (2002). "Glycogen Synthase Kinase-3J3 Modulates Notch Signaling and Stability." Current Biology, vol. 12, No. 12, pp. 1006-1011.
Fu et al. (2008). "SM16, an Orally Active TFG-f3 Type I Receptor Inhibitor Prevents Myofibroblast Induction and Vascular Fibrosis in the Rat Carotid Injury Model." Arteriosclerosis, Thrombosis and Vascular Biology, vol. 28, No. 4, pp. 665-671.
Fujioka et al. (2011). "Development of Auditory-Specific Brain Rhythm in Infants," European Journal of Neuroscience, 33:521-529.
Fujioka et al. (2015). "Manipulating cell fate in the cochlea: a feasible therapy for hearing loss." Trends Neurosci. 38, 139-44.

(56) References Cited

OTHER PUBLICATIONS

Fuller et al. (2012). "Intestinal crypts reproducibly expand in culture", J. Surg. Res., 178(1): 48-54.
Gale et al. (2010). "Cochlear Supporting Cells," Chapter 11 in Oxford Handbook of Auditory Science: The Ear, 31 pages.
Garcia-Berrocal Jr. et al. (2006). "Alternatives to Systemic Steroid Therapy for Refractory Immune-Mediated Inner Ear Disease: A Physiopathologic Approach." Eur. Arch. Otorhinolarynqol. vol. 263, No. 11, pp. 977-982.
Gellibert et al. (2004). "Identification of 1,5-Naphthyridine Derivatives as a Novel Series of Potent and Selective TGF-Beta Type 1 Receptor Inhibitors." J. Med. Chem. vol. 47, No. 18, pp. 4494-4506.
Gupta et al. (2006). "Fast-Gelling Injectable Blend ofHyaluronan and Methylcellulose for Intrathecal, Localized Delivery to the Injured Spinal Cord." Biomaterials, 27: 2370-2379.
Haegebarth et al. (2009). "Wnt Signaling, Lgr5, and Stem Cells in the Intestine and Skin." The American Jounral of Pathology. vol. 174, No. 3, pp. 715-721.
Haggarty et al. (2003). "Domain-Selective Small-Molecule Inhibitor ofHistone Deacetylase 6 (HDAC6)-Mediated Tubulin Deacetylation", Proc. Nat 'l. Acad Sci. USA, 100(8): 4389-4394.
Halder et al. (2005). "A Specific Inhibitor of TGF-f3 Receptor Kinase, SB-431542, as a Potent Antitumor Agent for Human Cancers." Neoplasia. vol. 7, No. 5, pp. 509-521.
Harding et al. (2005). "The effect of an age-related hearing loss gene (Ahl) on noise induced hearing loss and cochlear damage from low-frequency noise." Hearing Research, 204: 90-100.
Herraiz et al. (2010). "Intratympanic Drug Delivery for the Treatment ofInner Ear Diseases," Acta Otorrinolaringologica Espanola, 61(3): 225-232.
Hirsh et al. (1952). "Development of Materials for Speech Audiometry." Journal of Speech, Language, and Hearing Research, 17(3), 321-337.
Hong et al. (1998). "Human Dynamin-Like Protein Interacts with the Glycogen Synthase Kinase 3f3." Biochem. Biophys. Res. Commun. vol. 249, No. 3, pp. 697-703.
Hoskison et al. (2013). "Drug Delivery to the Ear," Therapeutic Delivery, 4(1): 115-124.
Hou et al. (2013). "Pluripotent Stem Cells Induced from Mouse Somatic Cells by Small-Molecule Compounds." Science. 341(6146): 651-654.
Huang et al. (2009). "Systematic and Integrative Analysis of Large Gene Lists Using DAVID Bioinformatics Resources," Nature Protocols, 4(1):44-57.
Huang et al. (2009). "RAD18 Transmits DNA Damage Signaling to Elicit Homologous Recombination Repair." Nat. Cell. Biol., vol. 11, No. 5, pp. 592-603.
Huang et al. (2009). "Directed, Efficient, and Versatile Modifications of the *Drosophila* Genome by Genomic Engineering." PNAS. vol. 106, No. 20, pp. 8284-9290.
International Search Report for Int'l Application No. PCT/US2014/023197, titled:"Compositions and Methods for Epithelial Stem Cell Expansion and Culture"; dated May 28, 2014.
International Preliminary Report on Patentability for Int'l Application No. PCT/US2014/023197, titled: "Compositions and Methods for Epithelial Stem Cell Expansion and Culture"; dated Sep. 15, 2015.
International Preliminary Report on Patentability for Int'l Application No. PCT/US2015/048442, titled: "Compositions, Systems, and Methods for Generating Inner Ear Hair Cells for Treatment of Hearing Loss"; dated Mar. 7, 2017.
Isaacson et al. (2003). "Differential Diagnosis and Treatment of Hearing Loss." American Family Physician. vol. 18, pp. 1125-1132.
Itoh et al. (2016). "False HDAC inhibition by aurone compound." Chemical and Pharmaceutical Bulletin, vol. 64, pp. 1124-1128.
Izumikawa et al. (2005). "Auditory Hair Cell Replacement and Hearing Improvement by Atohl Gene Therapy in Deaf Mammals." Nat Med., 11(3): 271-276.

Jadali et al. (2016). "Activation of PI3K signaling prevents aminoglycoside-induced hair cell death in the murine cochlea", Biology Open,vol. 5, No. 6, 03, p. 698-708, XP055630999.
Jeon et al. (2011). "Notch Signaling Alters Sensory or Neuronal Cell Fate Specification OfInner Ear Stem Cells." Journal Neurosci. vol. 31, No. 23, pp. 8351-8358.
Jung et al. (2011). "Isolation and in vitro expansion of human colonic stem cells," Nat. Med., 17, 1225-1227.
Kanzaki et al. (2012). "Novel in Vivo Imaging Analysis of an Inner Ear Drug Delivery System in Mice: Comparison of Inner Ear Drug Concentrations OverTimeAfter Transtympanic and Systemic Injections." PloS One, vol. 7:e48480.
Kawamoto, T. (2003). "Use of a New Adhesive Film for the Preparation of Multi-Purpose Fresh-Frozen Sections from Hard Tissues, Whole-Animals, Insects and Plants." Arch. Histol. Cytol. vol. 66, No. 2, pp. 123-143.
Kazanjian et al. (2010). "Atonal homolog 1 is required for growth and differentiation effects of notch/gamma-secretase inhibitors on normal and cancerous intestinal epithelial cells," Gastroenterology, 139: 918-928.
Kim et al. (2015). "Development of a Drug Delivery System for the Inner Ear Using Poly(amino acid)-Based Nanoparticles," Drug Delivery, 22(3): 367-374.
Kimmel. (1987). "Identification and Characterization of Specific Clones: Strategy for Confirming the Validity of Presumptive Clones", Methods Enzymol. vol. 152, p. 507-511.
Koch et al. (2013). "Stem cells living with a Notch." The Company of Biologists Ltd. Development, vol. 140, pp. 689-704.
Kujavva et al. (1997). "Conditioning-Related Protection from Acoustic Injury: Effects of Chronic Deefferentation and Sham Surgery," J. Neurophysiol., vol. 78, pp. 3095-3106.
Kuo et al. (2015). "In Vivo Cochlear Hair Cell Generation and Survival by Coactivation of beta-Catenin and Atohl." Journal of Neuroscience, vol. 35, No. 30, p. 10786-10798.
Lajud et al. (2013). "A Regulated Delivery System for Inner Ear Drug Application," Journal of Controlled Release: Official Journal of the Controlled Release Society, 166:268-276.
Lanford et al. (1999). "Notch Signaling Pathway Mediates Hair Cell Development in Mammalian Cochlea." Nature Genetics. vol. 21, pp. 289-292.
Lasak et al. (2014). "Hearing Loss: Diagnosis and Management." Primary Care, vol. 41, pp. 19-31.
Lehiste et al. (1959). "Linguistic considerations in the study of speech intelligibility." Journal of the Acoustical Society of America 31 (3): 280-286.
Lehner et al. (1997). "A Totally Implantable Drug Delivery System for Local Therapy of the Middle and Inner Ear." Ear, Nose, & Throat Journal, 76(8):567-570.
Li et al. (1998). "Interaction of Glycogen Synthase Kinase 3(3 with the DF3/MUC1 Carcinoma-Associated Antigen and f3-Catenin." Molecular and Cellular Biology, vol. 18, No. 12, pp. 7216-7224.
Li et al. (2003). "Pluripotent stem cells from the adult mouse inner ear", Nature Medicine. vol. 9, No. 10, p. 1293-1299.
Li et al. (2003). "Retinoic Acid Stimulates Chondrocyte Differentiation and Enhances Bone Morphogenetic Protein Effects through Induction of Smadl and Smad5." Endocrinology. vol. 144, No. 6, pp. 2514-2523.
Li et al. (2010). "Generation of iPSCs from mouse fibroblasts with a single gene, Oct. 4, and small molecules." Cell Research. 21(1): 196-204.
Li et al. (2013). "A Novel Aerosol-Mediated Drug Delivery System for Inner Ear Therapy: Intratympanic Aerosol Methylprednisolone Can Attenuate Acoustic Trauma," IEEE Transactions on Bio-Medical Engineering, 60(9): 2450-2460.
Li et al. (2017). "Advances in nano-based inner ear delivery systems for the treatment of sensorineural hearing loss." Adv. Drug Deliv. Rev. 108, 2-12.
Liberman et al. (2017). "Cochlear synaptopathy in acquired sensorineural hearing loss: Manifestations and mechanisms." Hearing research. 349:138-47.
Lin et al. (2011). "Inhibition of Notch Activity Promotes Nonmitotic Regeneration of Hair Cells in the Adult Mouse Utricles," The Journal of Neurosciencce, vol. 31, No. 43, pp. 15329-15339.

(56) References Cited

OTHER PUBLICATIONS

Liu et al. (2012). "In vivo Notch reactivation in differentiating cochlear hair cells induces Sox2 and Prox1 expression but does not disrupt hair cell maturation." Dev Dyn., vol. 241, pp. 684-696.
Liu et al (2015). "Identification of Stage-Specific Markers During Differentiation of Hair Cells From Mouse Inner Ear Stem Cells or Progenitor Cells in Vitro." Int. J. Biochem. Cell. Biol., vol. 60, pp. 99-111.
Lu et al. (2008). "The Influence of Glycogen Synthase Kinase 3 in Limiting Cell Addition in the Mammalian Ear," pp. 1059-1075, published online in Wiley InterScience (www.interscience.wiley.com).
Lukacs et al. (2010). "Isolation, cultivation and characterization of adult murine prostate stem cells," Nat. Protoc., 5(4):702-713.
Lumpkin et al. (2003). "Math1-Driven GFP Expression in the Developing Nervous System of Transgenic Mice," Gene Expr Patters, 3(4): 389-395.
Maison et al. (2003). "Olivocochlear Innervation in the Mouse: munocytochemical Maps, Crossed Versus Uncrossed Contributions, and Transmitter Colocalization." J. Comp. Neural., vol. 455, No. 3, pp. 406-416.
Mak et al. (2003). "The Tuberin-Hamartin Complex Negatively Regulates ,8-Catenin Signaling Activity." The Journal of Biological Chemistry. vol. 278, No. 8, 5947-5951.
Martinez-Monedero et al. (2008). "Differentiation of Inner Ear Stem Cells to Functional Sensory Neurons." Developmental Neurobiology. vol. 68, No. 5, pp. 669-684.
McCall et al. (2010). "Drug Delivery for Treatment of Inner Ear Disease: Current State of Knavvledge." Ear and Hearing, vol. 31, No. 2, pp. 156-165.
McLean et al. (2017). "Clonal Expansion of Lgr5-Positive Cells from Mammalian Cochlea and High-Purity Generation of Sensory Hair Cells." Cell Reports,vol. 18, No. 8, p. 1917-1929.
Mendel et al. (2014). "Normative data for the Maryland CNC Test. Journal of the American Academy of Audiology." 25, 775-781.
Meng et al. (2009). "Gamma-Secretase Inhibitors Abrogate Oxaliplatin-Induced Activation of the Notch-1 Signaling Pathway in Colon Cancer Cells Resulting in Enhanced Chemosensitivity." Cancer Research. vol. 69, pp. 573-582.
Mikulec et al. (2008). "Permeability of the Round Window Membrane is Influenced by the Composition of Applied Drug Solutions and by Common Surgical Procedures." Otol. Neurotol. vol. 29, No. 7, pp. 1020-1026.
Mills, D.M. (2006). "Determining the Cause of Hearing Loss: Differential Diagnosis Using a Comparison of Audiometric and Otoacoustic Emission Responses," Ear and Hearing, 27(5):508-525.
Mimasu et al. (2008). "Crystal structure of histone demelhylase LSD1 and tranylcypromine at 2.25 A," Biochemical and Biophysical Research ommunications, vol. 366, pp. 15-22.
Mimura et al. (2006). "Topical Ocular Drug Delivery to Inner Ear Disease and Sinusitis," Southern Medical Journal, 99(11): 1287-1289.
Mittal et al. (2017). "Recent advancements in the regeneration of auditory hair cells and hearing restoration." Frontiers in molecular neuroscience. 10:236.
Mizutari et al. (2013). "Notch Inhibition Induces Cochlear Hair Cell Regeneration and Recovery of Hearing after Acoustic Trauma." Neuron, vol. 77, No. 1, pp. 58-69.
Mizutari et al. (2014). "Spontaneous Recovery of Cochlear Fibrocytes After Severe Degeneration Caused by Acute Energy Failure." Frontiers in Phamcacology, vol. 5, No. 198, pp. 1-3.
Mundada et al. (2009). "In Situ Gelling Polymers in Ocular Drug Delivery Systems: A Review," Critical Reviews in Therapeutic Drug Carrier Systems, 26(1):85-118. (Impact Factor-3.99).
Nakagawa et al. (2011). "Local Drug Delivery to the Inner Ear Using Biodegradable Materials," Therapeutic Delivery, 2(6):807-814.
Nakamura et al. (1998). "Axin, An Inhibitor of the Wnt Signalling Pathway, Interacts ,vith f3-Catenin, GSK-3(3 and APC and Reduces the f3-Catenin Level." Genes Cells, vol. 3, No. 6, pp. 395-403.

Nekrassov et al. (2006). "Additive effects of antiepileptic drugs and pentylenetetrazole on hearing." Neuroscience Letters. 406(3): 276-80.
Olsauskas-Kuprys et al. (2013). "Gamma Secretase Inhibitors of Notch Signaling." OncoTargets and Therapy, vol. 6, pp. 943-955.
Oshima et al. (2007). "Phylogenetic Relationships Among Mycoplasmas Based on the Whole Genomic Information," J. Mol. Evol., 65(3):249-258.
Paasche et al. (2003). "Technical Report: Modification of a Cochlear Implant Electrode for Drug Delivery to the Inner Ear," Otology & Neurotology, 24:222-227.
Pararas et al. (2011). "Kinetics of Reciprocating Drug Delivery to the Inner Ear." Journal of Controlled Release: Official Journal of the Controlled Release Society, 152:270-277.
Pararas et al. (2012). "Microsystems Technologies for Drug Delivery to the Inner Ear," Advanced Drug Delivery Reviews, 64:1650-1660.
Park et al. (2009). "Selective GSK-3? inhibitors attenuate the cisplatin-induced cytotoxicity of auditory cells." Hearing research. 257(1-2): 53-62.
Paulson et al. (2008). "A Novel Controlled Local Drug Delivery System for Inner Ear Disease," Otology/Basic and Clinical Research; The Laryngoscope, vol. 118:706-711.
Peer et al. (2007). "Nanocarriers as an Emerging Platform for Cancer Therapy," Nature Nanotechnology, 2:751-760.
Peterson et al. (1962). "Revised CNC lists for auditory tests." Journal of Speech and Hearing Disorders 27:62-70.
Peterson et al. (2008). "Oral Administration of GW788388, An Inhibitor of TGF-f3 Type I and II Receptor Kinases, Decreases Renal Fibrosis." Kidney International, vol. 73, pp. 705-715.
Plontke et al. (2002). "Pharmacokinetic Considerations in Intratympanic Drug Delivery to the Inner Ear," Acta Oto-Rhino-Laryngologica Belgica, 56(4): 369-370.
Plontke et al. (2002). Transtympanic Endoscopy for Drug Delivery to the Inner Ear Using a New Microendoscope/ Advances in Oto-Rhino-Laryngology, 59: 149-155.
Plontke et al. (2004). "ID-and 3D-Computer Simulation for Experimental Planning and Interpretation of Pharmacokinetic Studies in the Inner Ear After Local Drug Delivery." Altex, vol. 21, Suppl 3, pp. 77-85.
Plontke et al. (2006). "Simulation of Application Strategies for Local Drug Delivery to the Inner Ear." ORL Journal for Oto-Rhino-Laryngology and Its Related Specialties. vol. 68, No. 6, pp. 386-392.
Plontke et al. (2006). "Technical Note on Microcatheter Implantation for Local Inner Ear Drug Delivery: Surgical Technique and Safety Aspects," Otology & Neurotology, 27(7):912-917.
Plontke et al. (2007). "Cochlear Pharmacokinetics With Local Inner Ear Drug Delivery Using a Three-Dimensional Finite-Element Computer Model." Audiology & Neuro-Otology, vol. 12, pp. 37-48.
Plontke et al. (2008). "Dexamethasone Concentration Gradients Along Scala Tympani After Application to the Round Window Membrane," Otology & Neurotology, 29(3):401-406.
Plontke et al. (2009). "Randomized Double Blind, Placebo Controlled Trial on the Safety and Efficacy of Continuous Intratympanic Dexamethasone Delivered Via a Round Window Catheter for Severe to Profound Sudden Idiopathic Sensorineural Hearing Loss After Failure of Systemic Therapy." The Laryngoscope, 119:359-369 (2009).
Plontke, S.K. (2011). "Evaluation of the Round Window Niche Before Local Drug Delivery to the Inner Ear Using a New Mini-Otoscope," Otology & Neurotology, 32(1):183-185.
Pritz et al. (2013). "Nanomedicine Strategies for Drug Delivery to the Ear." Nanomedicine, 8(7): 1155-1172.
Provenzano et al. (2007). "A role for epigenetics in hearing: Establishment and maintenance of auditory specific gene expression patterns," Hearing Res., 233(1-2): 1-13.
Purow, B. (2012). "Notch Inhibition as a Promising New Approach to Cancer Therapy," Advances in Experimental Medicine and Biology, 727:305-319.
Ramakers et al. (2015). "The effect of cochlear implantation on tinnitus in patients with bilateral hearing loss: A systematic review." Laryngoscope 125, 2584-92.

(56) References Cited

OTHER PUBLICATIONS

Raman et al. (2011). "Effectiveness of Cochlear Implants in Adults with Sensorineural Hearing Loss." Agency for Healthcare Research and Quality (US).
Raphael, Y. (1992). "Evidence for Supporting Cell Mitosis in Response to Acoustic Trauma in the Avian Inner Ear." Journal of Neurocytology, 21:663-671.
Richardson et al. (2008). "Novel Drug Delivery Systems for Inner Ear Protection and Regeneration After Hearing Loss," Expert Opinion on Drug Delivery, 5(10): 1059-1076.
Rivera et al. (2012). "Drug Delivery to the Inner Ear: Strategies and their Therapeutic Implications for Sensorineural Hearing Loss," Current Drug Delivery, 9(3): 231-242.
Roccio et al. (2015). "Cell cycle reactivation of cochlear progenitor cells in neonatal FUCCI mice by a GSK3 small molecule inhibitor." Scientific reports. 5: 17886.
Roche et al. (2015). "On the Horizon: Cochlear implant technology." Otolaryngol. Clin. North Am. 48, 1097-116.
Roy et al. (2010). "Cell-Specific Targeting in the Mouse Inner Ear Using Nanoparticles Conjugated with a Neurotrophin-Derived Peptide Ligand: Potential Tool for Drug Delivery," International Journal of Pharmaceutics, 390: 214-224.
Roy et al. (2012). "Strategies for Drug Delivery to the Human Inner Ear by Multifunctional Nanoparticles," Nanomedicine, 7(1):55-63.
Ryals et al. (2013). "Return of Function After Hair Cell Regeneration," Hearing Research, 297: 113-120.
Sage et al. (2005). "Proliferation of Functional Hair Cells in Vivo in the Absence of the Retinoblastoma Protein." Science. vol. 307, pp. 1114-1118.
Sage et al. (2006). "Essential role of retinoblastoma protein in mammalian hair cell development and hearing." Proc. Natl. Acad. Sci. USA. vol. 103, pp. 7345-7350.
Sakamoto et al. (2010). "Inner Ear Drug Delivery System from the Clinical Point of View." Acta Oto-Laryngologica, 130:sup563: 101-104.
Salt et al. (2005). "Local Inner Ear Drug Delivery and Phannacokinetics." Drug. Discov. Today, vol. 10, No. 19, pp. 1299-1306.
Salt et al. (2008). "Dependence of Hearing Changes on the Dose of intratympanically Applied Gentamicin: A Meta-Analysis Using Mathematical Simulations of Clinical Drug Delivery Protocols." The Laryngoscope, 118(10): 1793-1800.
Salt et al. (2008). "Dexamethasone Concentration Gradients Along Scala Tympani After Application to the Round Windmv Membrane," Otology & Neurotology, 29(3):401-406.
Salt et al. (2009). "Principles of Local Drug Delivery to the Inner Ear." Audiol. Neurotol. vol. 14, No. 6, pp. 350-360.
Salt, A. (2010). "Guest Editorial: Drug Delivery for Treatment of Inner Ear Disease: Current State of Knowledge." Ear and Hearing, vol. 31, p. 155.
Salt et al. (2011). "Distribution of Dexamethasone and Preservation of Inner Ear Function Following Intratympanic Delivery of a Gel-Based Formulation." Audiology & Neuro-otology, vol. 16, pp. 323-335.
Salvi et al. (2008). "Hair Cell Regeneration, Repair, and Protection." Springer Handbook of Auditory Research. vols. 1-33, 323.
Sataloff, et al. (2001). "Differential Diagnosis of Occupational Hearing Loss." Occupational Health & Safety, 70(9): 126-129.
Sato et al. (2011). "Long-term expansion of epithelial organoids from human colon, adenoma, adenocarcinoma, and Barrett's epithelium," Gastroenterology, 141: 1762-1772.
Sato et al. (2011). "Paneth cells constitute the niche for Lgr5 stem cells in intestinal crypts," Nature, 469: 415-418.
Sawyer et al. (2003). "Synthesis and Activity of New Aryl-and Heteroaryl-Substituted Pyrazole Inhibitors of the Transforming Gro'''1h Factor-Beta Type 1 Receptor Kinase Domain." J. Med. Chem., vol. 46, No. 19, pp. 3953-3956.
Sawyer et al. (2004). "Synthesis and Activity of New Aryl- and Heteroaryl-Substituted 5, 6-Dihiydro-4HPyrrolo[1,2-b]Pyrazole Inhibitors of the Transforming Growth Factor-Beta Type I Receptor Kinase Domain," Bioorg. Med. Chem. Lett., vol. 14, No. 13, pp. 3581-3584.
Schwarz-Romond et al. (2002). "The Ankyrin Repeat Protein Diversin Recruits Casein Kinase le to the f3-Catenin Degradation Complex and Acts in Both Canonical Wnt and Wnt/JNK Signaling." Genes, Dev., vol. 16, No. 16, pp. 2073-2084.
Scoville et al. (2008). "Current view: intestinal stem cells and signaling," Gastroenterology, 134(3): 849-864.
Seidman, M.D. (1998). "Glutamate Antagonists, Steroids, and Antioxidants as Therapeutic Options for Hearing Loss and Tinnitus and the Use of an Inner Ear Drug Delivery System." The International Tinnitus Journal, vol. 4, pp. 148-154.
Sekine et al. (2006). "Hath1 Up-Regulates Gastric Mucin Gene Expression in Gastric Cells." Biochem. Biophys. Res. Commun., 344(4): 1166-71.
Shariatmadari et al. (2005). "Increased Wnt Levels in the Neural Tube Impair the Function of Adherens Junctions During Neurulation," Mol Cell Neurosci.,30(3): 437-51. Epub (abstract only).
Shi et al. (2010). "Beta-Catenin Up-Regulates Atoh1 Expression in Neural Progenitor Cells by Interaction with an Atoh1 3' Enhancer." The Journal of Biological Chemistry, vol. 285, pp. 392-400.
Shi et al. (2012). "Wnt-Responsive Lgr5-Expressing Stem Cells are Hair Cell Progenitors in the Cochlea." J Neuroscience, 32 (28): 9639-9648.
Shi et al. (2013). "Generation of Hair Cells in Neonatal Mice by f3-Catenin Overexpression in Lgr5-Positive Cochlear Progenitors." Proc Natl Acad Sci USA, vol. 110, No. 34, pp. 13851-13856.
Shih et al. (2007). "Notch Signaling, Gamma-Secretase Inhibitors, and Cancer Therapy." Cancer Research, vol. 67, pp. 1879-1882.
Shoichet et al. (2007). "Intrathecal Drug Delivery Strategy is Safe and Efficacious for Localized Delivery to the Spinal Cord," Progress in Brain Research, 161:385-392.
Snippert et al. (2010). "Intestinal crypt homeostasis results from neutral competition between symmetrically dividing Lgr5 stem cells," Cell, 143: 134-144.
Staecker et al. (2004). "Drug Delivery to the Inner Ear Using Gene Therapy," Otolaryngologic Clinics of North America, vol. 37, pp. 1091-1108.
Staecker et al. (2013). "Developments in Delivery of Medications for Inner Ear Disease," Expert Opinion on Drug Delivery, 10(5): 639-650.
Surovtseva et al. (2012). "Prestin Binding Peptides as Ligands for Targeted Polymersome Mediated Drug Delivery to Outer Hair Cells in the Inner Ear," International Journal of Pharmaceutics, 424: 121-127.
Swan et al. (2008). "Inner Ear Drug Delivery for Auditory Applications." Adv. Drug. Deliv. Rev., vol. 60, No. 15, pp. 1583-1599.
Tillman et al. (1966). "An expanded test for speech discrimination utilizing CNC monosyllabic words: Northwestern University Auditory Test No. 6." Northwestern Univ Evanston 11 Auditory Research Lab.
Tojo et al. (2005). "The ALK-5 Inhibitor A-83-01 Inhibits Smad Signaling and Epithelial-to-Mesenchymal Transition by Transforming Growth Factor-f3." Cancer Sci., vol. 96, No. 11, pp. 791-800.
Valdimarsdottir et al. (2005). "Functions of the TGFf3 Superfamily in Human Embryonic StempCells." APMIS. vol 113, pp. 773-389.
Van Der Flier et al. (2009). "Stem cells, self-renewal, and differentiation in the intestinal epithelium," Annual Review of Physiology, 71: 241-260.
Van Dussen et al. (2012). "Notch signaling modulates proliferation and differentiation of intestinal crypt base columnar stem cells." The Company of Biologists Ltd., Development 139, pp. 488-497.
Van Es et al. (2005). "Notch/gamma-secretase inhibition turns proliferative cells in intestinal crypts and adenomas into goblet cells," Nature, 435: 959-963.
Van Es et al. (2010). "Intestinal stem cells lacking the Math1 tumour suppressor are refractory to Notch inhibitors." Nat. Commun., 1(18): 1-5.
Van Tomme et al. (2008). "In Situ Gelling Hydrogels for Phannaceutical and Biomedical Applications." Int. J. Pharm., 355(1-2): 1-18.

(56) References Cited

OTHER PUBLICATIONS

Von Kries et al. (2000). "Hot Spots in Beta-Catenin for Interactions with LEF-1, Conductin and APC." Nat. Struct. Biol., vol. 7, No. 9, pp. 800-807.

Voytik-Harbin et al. (1998). "Small Intestinal Submucosa: A Tissue-Derived Extracellular Matrix That Promotes Tissue-Specific Growth and Differentiation of Cells in Vitro." Tissue Engineering, 4(2): 157-174.

Wahl et al. (1987). "Molecular Hybridization of Nucleic Acids", Methods in Enzymology. vol. 152, p. 399-407.

Wang et al. (2002). "Dynamics of Noise-Induced Cellular Injury and Repair in the Mouse Cochlea," J. of the Assoc. of Research in Otolaryngology, 3:248-268.

Wang et al. (2004). "Suppression of Androgen Receptor-Mediated Transactivation and Cell Growth by the Glycogen Synthase Kinase 3β in Prostate Cells." Journal of Biological Chemistry, vol. 279, No. 31, pp. 32444-32452.

Warchol et al. (1996). "Regenerative Proliferation in Organ Cultures of the Avian Cochlea: Identification of the Initial Progenitors and Determination of the Latency of the Proliferative Response." The Journal of Neuroscience: the Official Journal of the Society for Neuroscience. vol. 16, pp. 5466-5477.

White et al. (2006). "Mammalian Cochlear Supporting Cells Can Divide and Trans-Differentiate Into Hair Cells." Nature, vol. 441, No. 7096, pp. 984-987.

Wilson et al. (2003). "A word-recognition task in multi-talker babble using a descending presentation mode from 24 dB to O dB signal to babble." Journal of Rehabilitation Research and Development, 40(4), 321-328.

Wise et al. (2012). "Drug Delivery to the Inner Ear." Journal of Neural Engineering, 9(6):065002, 10 pages.

Wong et al. (2015). "Mechanisms of sensorineural cell damage, death and survival in the cochlea." Frontiers in Aging Neuroscience. vol. 7, Article 58, pp. 1-15.

Written Opinion of the International Searching Authority for Int'l Application No. PCT/US2014/023197, titled: "Compositions and Methods for Epithelial Stem Cell Expansion and Culture"; dated May 28, 2014.

Wu et al. (2004). Modulation of Notch Signaling by Mastermind-Like (MAML) Transcriptional Co-Activators and Their Involvement in Tumorigenesis/ Seminars in Cancer Biology, 14: 348-356.

Yang et al. (2012). "Functional Features of Trans-Differentiated Hair Cells Mediated by Atoh1 Reveals a Primordial Mechanism." J. ofNeuroscience, 32(11):3712-3725.

Yang et al. (2013). "Ectopic Hair Cell-Like Cell Induction by Math! Mainly Involves Direct Transdifferentiation in Neonatal Mammalian Cochlea," Neuroscience Letters, 549:7-11.

Yao et al. (2010). "Prostate-regenerating capacity of cultured human adult prostate epithelial cells," Cells Tissues Organs, 191: 203-212.

Yilmaz et al. (2012). "mTORCl in the Paneth cell niche couples intestinal stem-cell function to calorie intake," Nature, 486: 490-495.

Yin et al. (2013). "Niche-Independent High-Purity Cultures ofLgr5+ Intestinal Stem Cells and Their Progeny." Nat. Methods, vol. 11, No. 1, pp. 106-112.

Ying et al. (2008). "The ground state of embryonic stem cell self-renewal," Nature, 453: 519-523.

Yingling et al. (2004). "Development of TGF-B Signalling Inhibitors for Cancer Therapy." Nature Reviews Drug Discovery. vol. 3, No. 12, pp. 1011-1022.

Yu et al. (2010). "In vivo proliferation of postmitotic cochlear supporting cells by acute ablation of the retinoblastoma protein in neonatal mice." J Neurosci, vol. 30, pp. 5927-5936.

Yuge et al. (2004). "Transplanted Human Amniotic Epithelial Cells Express Connexin 26 and Na-Kadenosine Triphophatase in the Inner Ear." Transplantation. vol. 77, No. 9, pp. 1452-1454.

Yui et al. (2012). "Functional engraftment of colon epithelium expanded in vitro from a single adult Lgr5+ stem cell," Nature Medicine, 18(4): 618-623.

Zahnert, T. (2011). "The Differential Diagnosis of Hearing Loss." Deutsches Arzteblatt International. vol. 108, pp. 433-443, quiz 44.

Zhang et al. (2003). "Inhibitory Phosphorylation of Glycogen Synthase Kinase-3 (GSK-3) in Response to Lithium," J. Bio. Chem., 278(3): 33067-33077.

Zhao et al. (2015). "A XEN-like State Bridges Somatic Cells to Pluripotency during Chemical Reprogramming." Cell. 163(7): 1678-1691.

Zheng et al. (2000). "Overexpresson of Math1 Induces Robust Production of Extra Hair Cells in Postnatal Rat Inner Ears," Nature Neuroscience, 3(6): 580-586.

Bowie et al. (1990). "Deciphering the message in protein sequences: tolerance to amino acid substitutions." Science. 247:1306-1310.

Burgess et al. (1990). "Possible dissociation of the heparin-binding and mitogenic activities of heparin-binding (acidic fibroblast) growth factor-1 from its receptor-binding activities by site-directed mutagenesis of a single lysine residue." J. Cell Biol. 111 :2129-2138.

Lazar et al. (1988). "Transforming growth factor alpha: mutation of aspartic acid 47 and leucine 48 results in different biological activities." Mol. Cell. Biol., 8:1247-1252.

Murillo-Cuesta et al. (2015). "Transforming growth factor β1 inhibition protects from noise-induced hearing loss." Frontiers in Aging Neuroscience. vol. 7, Article 32, pp. 1-13.

Suenaga et al. (2013). "Bmp4 expressed in preadipocytes is required for the onset of adipocyte differentiation." Cytokine 64.1 138-145.

Zheng et al. (1997). "Induction of cell proliferation by fibroblast and insulin-like growth factors in pure rat inner ear epithelial cell cultures." Journal of Neuroscience. 17(1): 216-26.

Kujawa et al. (1994). "ATP antagonists cibacron blue, basilen blue and suramin alter sound-evoked responses of the cochlea and auditory nerve." Hearing Research. vol. 78 pp. 181-188.

Liu et al. (2013). "Current Strategies for Drug Delivery to the Inner Ear." Acta Pharmaceutica Sinica B 2013; 3(2): 86-96.

Lyu et al. (2014). "Differentiation of Rabbit Bone Mesenchymal Stem Cells into Islet Cells by 5-Azacytidine in vitro." Acta Veterinaria et Zootechnica Sinica, 45(9): 1538-1543. (Abstract only).

McLean et al. (2016). "Distinct capacity for differentiation to inner ear cell types by progenitor cells of the cochlea and vestibular organs." Development. 143(23): 4381-93.

Van Landeghem et al. (2012). "Activation of two distinct Sox9-EGFP-expressing intestinal stem cell populations during crypt regeneration after irradiation." Am J Physiol Gastrointest Liver Physiol 302:G1111-G1132.

White. (2016). "The Role of the Transcription Factor Foxo3 in Hearing Maintenance: Informed Speculation on a New Player in the Cochlea." Biomed Res Int. Article ID 1870675, 10 pages.

\* cited by examiner

COMPOSITIONS AND METHODS FOR GENERATING HAIR CELLS BY DOWNREGULATING FOXO

RELATED APPLICATIONS

This application claims priority to U.S. Patent Application No. 62/719,273, filed Aug. 17, 2018, the contents of which are herein incorporated by reference in their entirety.

FIELD OF THE INVENTION

The present disclosure relates to compositions and methods comprising a FOXO inhibitor for increasing proliferation of Lgr5+ cochlear cells, and related methods of treating hearing loss.

BACKGROUND OF THE INVENTION

Sensorineural hearing loss (SNHL), which is largely due to the loss of sensory hair cells and their neural connections is a widespread problem. It is estimated that over one billion young people are at risk for noise-related sensorineural hearing loss. The underlying pathophysiologic changes of the inner ear in these patients include damage to sensory transducers of the cochlea called hair cells. Hair cells are susceptible to damage, and although other species such as birds, fish, and amphibians can regenerate these cells throughout life, mammals lack this ability (Fujioka et al., Trends Neurosci. 38, 139-44, 2015).

SNHL accounts for about 90% of all hearing loss (Li et al., Adv. Drug Deliv. Rev. 108, 2-12, 2017), and leading causes include advanced age, ototoxic medications, and noise exposure (Liberman & Kujawa, Hear. Res. 349, 138-147, 2017). The majority of children and adults with SNHL are managed with hearing aids or cochlear implants, as there is currently no therapeutic option to restore function in the damaged inner ear (see, for example, Ramakers et al., Laryngoscope 125, 2584-92, 2015; Raman et al., Effectiveness of Cochlear Implants in Adults with Sensorineural Hearing Loss. Agency for Healthcare Research and Quality (US), 2011; and Roche & Hansen, Otolaryngol. Clin. North Am. 48, 1097-116, 2015). Thus, there is a need in the art for effective therapies for treating SNHL and related conditions.

SUMMARY OF THE INVENTION

In various aspects, the invention provides methods for increasing proliferation of a Lgr5+ cochlear cell.

The disclosure provides a method for increasing proliferation of a cochlear supporting cell or a vestibular supporting cell, comprising contacting the cell with a composition comprising a Forkhead box-O transcription factor (FOXO) inhibitor, thereby increasing Lgr5+ cochlear cell proliferation compared to a vehicle control.

The disclosure provides a method of producing an expanded population of cochlear supporting cell or a vestibular supporting cell, comprising contacting the population of cells with a composition comprising a Forkhead box-O transcription factor (FOXO) inhibitor, thereby producing an expanded population of cells, wherein the expanded population is capable of differentiating into hair cells as measured in a stem cell differentiation assay.

In some embodiments of the methods of the disclosure, FOXO inhibiter is AS184285. In some embodiments of the methods of the disclosure, further comprises contacting the cell with an HDAC inhibitor. In some embodiments of the methods of the disclosure, the HDAC inhibitor is Valproic Acid (VPA). In some embodiments of the methods of the disclosure, the cochlear supporting cell(s) or vestibular supporting cell(s) express(es) leucine-rich repeat-containing G-protein coupled receptor 5 (Lgr5).

In some embodiments of the methods of the disclosure, the cochlear supporting cell(s) or vestibular supporting cell(s) are/is a mature cell(s). In some embodiments of the methods of the disclosure, the expanded population of cochlear or vestibular cells expresses leucine-rich repeat-containing G-protein coupled receptor 5 (Lgr5). In some embodiments of the methods of the disclosure, the cochlear supporting cell(s) or vestibular supporting cell(s) are/is a cochlear supporting cell(s). In some embodiments of the methods of the disclosure, the expanded population of cochlear or vestibular cells are cochlear cells.

The disclosure provides a method of treating a subject who has, or is at risk of, developing an inner ear hearing or balance disorder, comprising administering to the subject: a Forkhead box-O transcription factor (FOXO).

In some embodiments of the methods of the disclosure, the subject has an inner ear hearing or balance disorder. In some embodiments of the methods of the disclosure, the disorder is an inner ear hearing disorder. In some embodiments of the methods of the disclosure, the disorder is a balance disorder. In some embodiments of the methods of the disclosure, the inner ear hearing or balance disorder is sensorineural hearing loss.

In some embodiments of the methods of the disclosure, the treatment results in improved auditory function when assessed by behavioral audiometry or auditory brainstem response (ABR) testing. In some embodiments of the methods of the disclosure, the increase of Lgr5+ cochlear cell proliferation compared to the vehicle control is measured in a stem cell proliferation assay. In some embodiments of the methods of the disclosure, contacting Lgr5$^+$ cochlear cells with the composition results in at least a 10-fold increase in the number of Lgr5$^+$ cochlear cell compared to the vehicle control. In some embodiments of the methods of the disclosure, contacting Lgr5$^+$ cochlear cells with the composition results in at least a 50-fold increase in the number of Lgr5$^+$ cochlear cell compared to the vehicle control.

In some embodiments of the methods of the disclosure, the resulting Lgr5$^+$ cochlear cells are capable of differentiating into hair cells as measured in a stem cell differentiation assay.

In some embodiments of the methods of the disclosure, the cochlear cell is in a cochlear tissue. In some embodiments of the methods of the disclosure, the Lgr5+ cochlear cell is contacted in vivo. In some embodiments of the methods of the disclosure, the Lgr5+ cochlear cell is a human Lgr5+ cochlear cell. In some embodiments of the methods of the disclosure, the Lgr5+ cochlear cell is a juvenile or an adult cell.

In some embodiments of the methods of the disclosure, the FOXO inhibitor is administered locally and/or systemically. In some embodiments of the methods of the disclosure, the FOXO inhibitor is administered locally. In some embodiments of the methods of the disclosure, the FOXO inhibitor is administered systemically. In some embodiments of the methods of the disclosure, the FOXO inhibitor is administered locally and systemically.

In some embodiments of the methods of the disclosure, the local administration is to the tympanic membrane, the middle ear or the inner ear. In some embodiments of the methods of the disclosure, the local administration is to the middle ear. In some embodiments of the methods of the disclosure, the systemic administration is oral or parenteral. In some embodiments of the methods of the disclosure, the systemic administration is oral.

The disclosure provides a pharmaceutical composition comprising a pharmaceutically acceptable carrier and a FOXO inhibitor; a FOXO inhibitor and an HDAC inhibitor.

In some embodiments of the compositions of the disclosure, the pharmaceutically-acceptable carrier is a biocompatible matrix. In some embodiments of the compositions of the disclosure, the biocompatible matrix comprises hyaluronic acid, hyaluronates, lecithin gels, pluronics, poly (ethyleneglycol), poloxamers, chitosans, xyloglucans, collagens, fibrins, polyesters, poly(lactides), poly(glycolide), poly(lactic-co-glycolic acid (PLGA), sucrose acetate isobutyrate, glycerol monooleate, poly anhydrides, poly caprolactone sucrose, glycerol monooleate, silk materials, or a combination thereof.

In some embodiments of the compositions of the disclosure, the biocompatible matrix is a gel or a foam. In some embodiments of the compositions of the disclosure, the pharmaceutically-acceptable carrier is a poloxamer. In some embodiments of the compositions of the disclosure, the poloxamer comprises at least one of Poloxamer 188 and Poloxamer 407 or mixtures thereof. In some embodiments of the compositions of the disclosure, the poloxamer is at concentration between about 5 wt % and about 25 wt %. In some embodiments of the compositions of the disclosure, the poloxamer is at concentration between about 10 wt % and about 23 wt % relative to the composition. In some embodiments of the compositions of the disclosure, the poloxamer is at concentration between about 15 wt % and about 20 wt % relative to the composition. In some embodiments of the compositions of the disclosure, the poloxamer is at a concentration of about 17 wt %.

In some embodiments of the compositions of the disclosure, the FOXO inhibitor is AS1842856. In some embodiments of the compositions of the disclosure, AS1842856 is at a concentration of about between 10 μM to 1,000,000 mM. In some embodiments of the compositions of the disclosure, the HDAC inhibitor is Valproic Acid (VPA). In some embodiments of the compositions of the disclosure, VPA is at a concentration of about between 10 mM and 10,000 mM. In some embodiments of the compositions of the disclosure, the composition formulated for local administration to the round window membrane. In some embodiments of the compositions of the disclosure, the composition formulated for transtympanic administration. In some embodiments of the compositions of the disclosure, the composition formulated administration to the middle ear and/or inner ear.

A method of treating a subject who has, or is at risk for developing, hearing loss, comprising administering to the subject a pharmaceutical composition comprising any one of the pharmaceutical compositions of the disclosure, in an amount sufficient to increase Lgr5+ cochlear cell proliferation. In some embodiments of the methods of the disclosure, the administration is transtympanically. In some embodiments, the administration results in improved auditory function.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION

Figure 1:
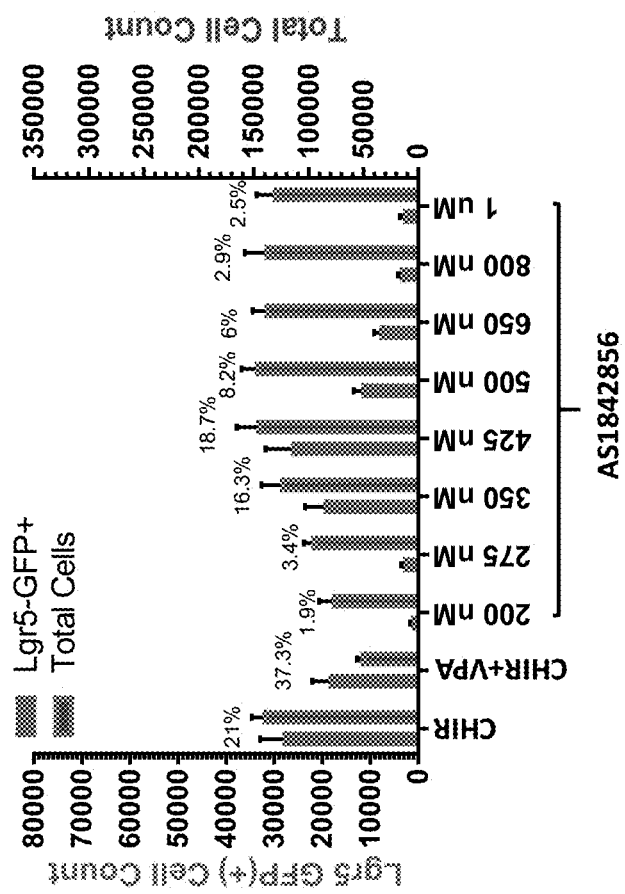
FIG. 1. displays the concentration-dependent effects of FOXO1 inhibitor AS1842856 on LGR5+ cell growth and enrichment in the background of EFI.

The invention is based upon the discovery that decreasing FOXO expression results in the proliferation of Lgr5+ cochlear cells while maintaining, in the daughter cells, the capacity to differentiate into cochlear hair cells.

Surprisingly, the methods described herein increase the proliferation of adult Lgr5+ cochlear cells Lgr5 (Leucine-rich repeat-containing G-protein coupled receptor 5) is a member of GPCR class A receptor proteins that is expressed across a diverse range of tissues such as in the muscle, placenta, spinal cord and brain, and particularly as a biomarker of adult stem cells in certain tissues. Lgr5+ stem cells are the precursors for sensory hair cells that line the cochlea. Cochlear hair cells, which do not regenerate, is a cause of hearing loss in a high percentage of the population.

Accordingly, the present invention provides composition and methods for inducing the self-renewal of a Lgr5+ cochlear cells by decreasing FOXO expression or activity. By self-renewal of Lgr5+ cochlear cells it is meant inducing the a Lgr5+ cochlear cell to proliferate while maintaining, in the daughter cells, the capacity to differentiate into cochlear hair cells.

Thus, in various aspects the invention provides method of increasing proliferation of a Lgr5+ cochlear cell; producing an expanded population of Lgr5+ cochlear cells and treating hearing loss in a subject by contacting a Lgr5+ cochlear cell or administering to the subject a decreasing FOXO. Optionally, the Lgr5+ cochlear cell is further contacted with or subject is further administered a HDAC inhibitor, such as valproic acid (VPA).

FOXO Inhibitors

Forkhead box-O transcription factor (FOXO) refers to a family of transcription factors that regulate the expression of genes involved in cell growth, proliferation, differentiation, and other processes. A feature of the FOX proteins is the forkhead box, a sequence of 80 to 100 amino acids forming a motif that binds to DNA. This forkhead motif is also known as the winged helix due to the butterfly-like appearance of the loops in the protein structure of the domain. Forkhead proteins are a subgroup of the helix-turn-helix class of proteins.

Exemplary FOXO transcription factors include FOXO1, FOXO3 (or FOXO3a), FOXO4, and FOXO6. Thus, a "FOXO inhibitor" refers to an agent that causes a decrease in the expression, levels, and/or activity of at least one FOXO gene, transcription factor protein, and/or pathway, for instance, in a cochlear cell. A "FOXO antagonist" refers to an agent that binds to at least one FOXO protein, and which optionally decreases, reduces, or otherwise eliminates binding of the FOXO protein by or to other molecules. Particular examples of FOXO inhibitors include AS1842856 and metformin.

In certain embodiments, a FOXO inhibitor decreases expression or activity of a FOXO transcription factor in a cochlear cell by about or at least about 10, 20, 30, 40, 50, 60, 70, 80, 90, 100, 150, 200, 250, 300, 350, 400, 450, or 500% or more relative to a vehicle control. Examples of these and related FOXO inhibitors include inhibitory nucleic acids (e.g., antisense, siRNA) agents which are directed against and decrease the expression of a FOXO gene/protein.

In some instances, a FOXO inhibitor decreases binding of a FOXO transcription factor to DNA in a cochlear cell by about or at least about 10, 20, 30, 40, 50, 60, 70, 80, 90, 100, 200, 300, 400, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to a vehicle control. In some embodiments, a FOXO inhibitor decreases nuclear localization of a FOXO transcription factor in a cochlear cell by about or at least about 10, 20, 30, 40, 50, 60, 70, 80, 90, 100, 200, 300, 400, or 500% or more relative to a vehicle control. In some embodiments, a FOXO inhibitor increases phosphorylation and optionally ubiquitination/degradation of a FOXO transcription factor in a cochlear cell by about or at least about 10, 20, 30, 40, 50, 60, 70, 80, 90, 100, 200, 300, 400, or 500% or more relative to a vehicle control. In some embodiments, a FOXO inhibitor increases acetylation of a FOXO transcription factor in a cochlear cell by about or at least about 10, 20, 30, 40, 50, 60, 70, 80, 90, 100, 200, 300, 400, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) relative to a vehicle control.

Methods of Use

In certain embodiments, the present disclosure relates to inducing, promoting, or enhancing the growth, proliferation or regeneration of inner ear tissue, particularly inner ear supporting cells and hair cells. Some embodiments relate to methods for controlled proliferation of stem cells comprising an initial phase of inducing stemness while inhibiting differentiation and a subsequent phase of differentiation of the stem cells into tissue cells.

When cochlear supporting cell populations are treated with an agent in accordance to the methods of the invention, whether the population is in vivo or in vitro, the treated supporting cells exhibit stem-like behavior in that the treated supporting cells have the capacity to proliferate and differentiate and, more specifically, differentiate into cochlear hair cells. In some instances, an agent induces and maintains the supporting cells to produce daughter stem cells that can divide for many generations and maintain the ability to have a high proportion of the resulting cells differentiate into hair cells. In certain embodiments, the proliferating stem cells express stem cell marker(s) selected from one or more of Lgr5, Sox2, Opeml, Phex, lin28, Lgr6, cyclin D1, Msx1, Myb, Kit, Gdnf3, Zic3, Dppa3, Dppa4, Dppa5, Nanog, Esrrb, Rex1, Dnmt3a, Dnmt3b, Dnmt31, Utf1, Tel1, Oct4, Klf4, Pax6, Six2, Zic1, Zic2, Otx2, Bmi1, CDX2, STATS, Smad1, smad2/3, smad4, smad5, and smad7.

In some embodiments, the methods may be used to maintain, or even transiently increase stemness (i.e., self-renewal) of a pre-existing supporting cell population prior to significant hair cell formation. In some embodiments, the pre-existing supporting cell population comprises inner pillar cells, outer pillar cells, inner phalangeal cells, Deiter cells, Hensen cells, Boettcher cells, and/or Claudius cells. Morphological analyses with immunostaining (including cell counts) and lineage tracing across a Representative Microscopy Samples may be used to confirm expansion of one or more of these cell-types. In some embodiments, the pre-existing supporting cells comprise Lgr5+ cells. Morphological analyses with immunostaining (including cell counts) and qPCR and RNA hybridization may be used to confirm Lgr5 upregulation amongst the cell population.

Advantageously, methods described herein can achieve these goals without the use of genetic manipulation. Germline manipulation used in many academic studies is not a therapeutically desirable approach to treating hearing loss. In general, the therapy preferably involves the administration of a small molecule, peptide, antibody, or other non-nucleic acid molecule or nucleic acid delivery vector unaccompanied by gene therapy. In certain embodiments, the therapy involves the administration of a small organic molecule. In some instances, hearing protection or restoration is achieved through the use of a (non-genetic) therapeutic that is injected in the middle ear and diffuses into the cochlea.

The cochlea relies heavily on all present cell types, and the organization of these cells is important to their function. As supporting cells play an important role in neurotransmitter cycling and cochlear mechanics. Thus, maintaining a rosette patterning within the organ of Corti may be important for function. Cochlear mechanics of the basilar membrane activate hair cell transduction. Due to the high sensitivity of cochlear mechanics, it is also desirable to avoid masses of cells. In all, maintaining proper distribution and relation of hair cells and supporting cells along the basilar membrane, even after proliferation, is likely a desired feature for hearing as supporting cell function and proper mechanics is necessary for normal hearing.

In some embodiments, the cell density of hair cells in a cochlear cell population is expanded in a manner that maintains, or even establishes, the rosette pattern characteristic of cochlear epithelia.

In certain embodiments, the cell density of hair cells is increased in a population of cochlear cells comprising both hair cells and supporting cells. The cochlear cell population may be an in vivo population (i.e., comprised by the cochlear epithelium of a subject) or the cochlear cell population may be an in vitro (ex vivo) population. If the population is an in vitro population, the increase in cell density may be determined by reference to a Representative Microscopy Sample of the population taken prior and subsequent to any treatment. If the population is an in vivo population, the increase in cell density may be determined indirectly by determining an effect upon the hearing of the subject with an increase in hair cell density correlating to an improvement in hearing.

In some embodiments, supporting cells placed in a Stem Cell Proliferation Assay in the absence of neuronal cells form ribbon synapses.

In a native cochlea, patterning of hair cells and supporting cells occurs in a manner parallel to the basilar membrane. In some embodiments, the proliferation of supporting cells in a cochlear cell population is expanded in a manner that the basilar membrane characteristic of cochlear epithelia.

In some embodiments, the number of supporting cells in an initial cochlear cell population is selectively expanded by treating the initial cochlear cell population with a composition of the present disclosure (e.g., a composition containing FOXO inhibitor) to form an intermediate cochlear cell population, wherein the ratio of supporting cells to hair cells in the intermediate cochlear cell population exceeds the ratio of supporting cells to hair cells in the initial cochlear cell population. The expanded cochlear cell population may be, for example, an in vivo population, an in vitro population or even an in vitro explant. In some embodiments, the ratio of supporting cells to hair cells in the intermediate cochlear cell population exceeds the ratio of supporting cells to hair cells in the initial cochlear cell population. For example, in some embodiments, the ratio of supporting cells to hair cells in the intermediate cochlear cell population exceeds the ratio of supporting cells to hair cells in the initial cochlear cell population by a factor of 1.1, 1.5, 2, 3, 4, 5 or more. In some instances, the capacity of a composition to expand a cochlear cell population is be determined by means of a Stem Cell Proliferation Assay.

In some embodiments, the number of stem cells in a cochlear cell population is expanded to form an intermediate cochlear cell population by treating a cochlear cell population with a composition of the present disclosure (e.g., a composition containing a FOXO inhbitor and optionally an HDAC inhibitor) wherein the cell density of stem cells in the intermediate cochlear cell population exceeds the cell density of stem cells in the initial cochlear cell population. The treated cochlear cell population may be, for example, an in vivo population, an in vitro population or even an in vitro explant. In one such embodiment, the cell density of stem cells in the treated cochlear cell population exceeds the cell density of stem cells in the initial cochlear cell population by a factor of at least 1.1, 1.25, 1.5, 2, 3, 4, 5 or more. In vitro cochlear cell populations may expand significantly more than in vivo populations; for example, in certain embodiments the cell density of stem cells in an expanded in vitro population of stem cells may be at least 4, 5, 6, 7, 8, 9, 10, 15, 20, 25, 30, 35, 40, 45, 50, 75, 100, 200, 300, 400, 500, 600, 700, 800, 900, 1000, 2000 or even 3000 times greater than the cell density of the stem cells in the initial cochlear cell population. In some instances, the capacity of a composition to expand a cochlear cell population is determined by means of a Stem Cell Proliferation Assay.

In some embodiments, a cochlea supporting cell population is treated with a composition of the present disclosure (e.g., a composition containing FOXO inhibitor and optionally an HDAC inhibitor) to increase the Lgr5 activity of the population. For example, in some instances a FOXO inhibitor has the capacity to increase and maintain the Lgr5 activity of an in vitro population of cochlea supporting cells by factor of at least 1.2, 1.5, 2, 3, 4, 5, or more. In some embodiments, the FOXO inhibitor has the capacity to increase the Lgr5 activity of an in vitro population of cochlea supporting cells by factor of 2, 3, 5 10, 100, 500, 1000, 2000 or even 3000. Increases in Lgr5 activity may also be observed for in vivo populations but the observed increase may be somewhat more modest. In some instances, the FOXO inhibitor has the capacity to increase the Lgr5 activity of an in vivo population of cochlea supporting cells by about or at least about 5%, 10%, 20%, 30% or more. In some instances, the capacity of the FOXO inhibitor for such an increase in Lgr5 activity is demonstrated, for example, in an In Vitro Lgr5+ Activity Assay, and in an in vivo population is demonstrated, for example, in an In Vivo Lgr5+ Activity Assay, as measured by isolating the organ and performing morphological analyses using immunostaining, endogenous fluorescent protein expression of Lgr5, and qPCR for Lgr5.

In addition to increasing the Lgr5 activity of the population, the number of Lgr5+ supporting cells in a cochlea cell population may be increased by treating a cochlea cell population containing Lgr5+ supporting cells (whether in vivo or in vitro) with a composition of the present disclosure. In general, the cell density of the stem/progenitor supporting cells may expand relative to the initial cell population via one or more of several mechanisms. For example, in some embodiments, newly generated Lgr5+ supporting cells may be generated that have increased stem cell propensity (i.e., greater capacity to differentiate into hair cell). By way of further example, in some embodiments no daughter Lgr5+ cells are generated by cell division, but pre-existing Lgr5+ supporting cells are induced to differentiate into hair cells. By way of further example, in some embodiments no daughter cells are generated by cell division, but Lgr5-supporting cells are activated to a greater level of Lgr5 activity and the activated supporting cells are then able to differentiate into hair cells. Regardless of the mechanism, in some embodiment a composition of the present disclosure (e.g., a composition comprising a PI3K agonist and optionally a second agent) has the capacity to increase the cell density of Lgr5+ supporting cells in an in vitro isolated cell population of cochlea supporting cells by factor of at least 5, 10, 50, 100, 500, 1000, or 2000. Increases in the cell density of Lgr5+ supporting cells may also be observed for in vivo populations but the observed increase may be somewhat more modest. For example, in some embodiments the composition (e.g., a composition comprising a FOXO inhibitor and optionally an HDAC inhibitor) has the capacity to increase the cell density of Lgr5+ supporting cells in an in vivo population of cochlea supporting cells by about or at least about 5%, 10%, 20%, 30% or more. The capacity of the composition (e.g., a composition comprising a FOXO inhibitor and optionally an HDAC inhibitor) for such an increase in Lgr5+ supporting cells in an in vitro population may be demonstrated, for example, in a Stem Cell Proliferation Assay or in an appropriate in vivo assay. In some embodiments, a composition of the present disclosure (e.g., a composition comprising a PI3K agonist and optionally a PI3K synergist or HDAC an inhibitor) has the capacity to increase the number of Lgr5+ cells in the cochlea by inducing expression of Lgr5 in cells with absent or low detection levels of the protein, while maintaining Native Morphology. In some embodiments, a composition (e.g., a composition comprising a FOXO inhibitor and optionally an HDAC inhibitor) has the capacity to increase the number of $Lgr5^+$ cells in the cochlea by inducing expression of Lgr5 in cells with absent or low detection levels of the protein, while maintaining Native Morphology and without producing Cell Aggregates.

Included in the invention are methods of increasing proliferation of a Lgr5+ cochlear cell by contacting a Lgr5+ cochlear cell with a FOXO inhibitor. Optionally, the cell is further contacted with an HDAC inhibitor.

In other embodiments, proliferation of an Lgr5+ cochlear cell is increased by contacting the cell with a FOXO inhibitor and an HDAC inhibitor.

In the various methods Lgr5+ cochlear cell proliferation is increased compared to a vehicle control.

In some embodiments, the FOXO inhibitor increases Lgr5+ cochlear cell proliferation by at least 10, 20, 30, 40, 50, 60, 70, 80, 90, 100, 150, 200, 250, 300, 350, 400, 450, or 500% or more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more), relative to a vehicle control. In some embodiments, the FOXO inhibitor in combination with an HDAC inhibitor increases Lgr5+ cochlear cell proliferation by at least 10, 20, 30, 40, 50, 60, 70, 80, 90, 100, 150, 200, 250, 300, 350, 400, 450, or 500% more (or at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more) than the FOXO inhibitor alone in a in a Stem Cell Proliferation Assay.

Also included are methods for expanding a population of cochlear cells in a cochlear tissue comprising a parent population of cells by contacting the cochlear tissue with a FOXO inhibitor to form an expanded population of cells in the cochlear tissue. The FOXO inhibitor (optionally in combination with an HDAC inhibitor is capable of (i) forming a proliferation assay final cell population from a proliferation assay initial cell population over a proliferation assay time period in a stem cell proliferation assay, and/or (ii) forming a differentiation assay final cell population from a differentiation assay initial cell population over a differentiation assay time period in a stem cell differentiation assay wherein: (a) the proliferation assay initial cell population has (i) a proliferation assay initial number of total cells, (ii) a proliferation assay initial number of Lgr5+ cells, (iii) a proliferation assay initial number of hair cells, (iv) a proliferation assay initial Lgr5+ cell fraction that equals the ratio of the proliferation assay initial number of Lgr5+ cells to the proliferation assay initial number of total cells, and (v) a proliferation assay initial hair cell fraction that equals the ratio of the proliferation assay initial number of hair cells to the proliferation assay initial number of total cells; (b) the proliferation assay final cell population has (i) a proliferation assay final number of total cells, (ii) a proliferation assay final number of Lgr5+ cells, (iii) a proliferation assay final number of hair cells, (iv) a proliferation assay final Lgr5+ cell fraction that equals the ratio of the proliferation assay final number of Lgr5+ cells to the proliferation assay final number of total cells and (v) a proliferation assay final hair cell fraction that equals the ratio of the proliferation assay final number of hair cells to the proliferation assay final number of total cells; (c) the differentiation assay initial cell population has (i) a differentiation assay initial number of total cells, (ii) a differentiation assay initial number of Lgr5+ cells, (iii) a differentiation assay initial number of hair cells, (iv) a differentiation assay initial Lgr5+ cell fraction that equals the ratio of the differentiation assay initial number of Lgr5+ cells to the differentiation assay initial number of total cells, and (v) a differentiation assay initial hair cell fraction that equals the ratio of the differentiation assay initial number of hair cells to the differentiation assay initial number of total cells; (d) the differentiation assay final cell population has (i) a differentiation assay final number of total cells, (ii) a differentiation assay final number of Lgr5+ cells, (iii) a differentiation assay final number of hair cells, (iv) a differentiation assay final Lgr5+ cell fraction that equals the ratio of the differentiation assay final number of Lgr5+ cells to the differentiation assay final number of total cells, and (v) a differentiation assay final hair cell fraction that equals the ratio of the differentiation assay final number of hair cells to the differentiation assay final number of total cells; (e) the proliferation assay final number of Lgr5+ cells exceeds the proliferation assay initial number of Lgr5+ cells by a factor of at least 10; and/or (f) the differentiation assay final number of hair cells is a non-zero number.

The invention also includes methods of producing an expanded population of Lgr5+ cochlear cells by contacting the cell population with a FOXO inhibitor. Optionally, the cells population is further contacted with an HDAC inhibitor.

The expanded population is capable of differentiating into hair cells as measured in a stem cell differentiation assay.

In some embodiments, the cochlear cell is in a cochlear tissue. In some embodiments, the cochlear tissue is in a subject.

Some embodiments relate to methods of treating a subject who has, or is at risk for developing, hearing loss or reduced auditory function. The prophylaxis and/or treatment of acute and chronic ear disease and hearing loss, dizziness and balance problems especially of sudden hearing loss, acoustic trauma, hearing loss due to chronic noise exposure, presbycusis, trauma during implantation of the inner ear prosthesis (insertion trauma), dizziness due to diseases of the inner ear area, dizziness related and/or as a symptom of Meniere's disease, vertigo related and/or as a symptom of Meniere's disease, tinnitus, and hearing loss due to antibiotics and cytostatics and other drugs.

Some embodiments include methods to prevent, reduce, or treat the incidence and/or severity of inner ear disorders and hearing impairments involving inner ear tissue, particularly inner ear hair cells, their progenitors, and optionally, the stria vascularis, and associated auditory nerves. Of particular interest are those conditions that lead to permanent hearing loss where reduced number of hair cells may be responsible and/or decreased hair cell function. Also of interest are those arising as an unwanted side-effect of ototoxic therapeutic drugs including cisplatin and its analogs, aminoglycoside antibiotics, salicylate and its analogs, or loop diuretics.

Hearing loss or reduced auditory function is treated or prevented in a subject by contacting a Lgr5+ cochlear cell or administering to the subject a FOXO inhibitor. Optionally, the Lgr5+ cochlear cell is further contacted with or subject is further administered an HDAC inhibitor Some embodiments include administering transtympanically to the subject. In some embodiments, administering results in improved hearing or auditory function in the subject.

Hearing loss or reduced auditory function is treated or prevented utilizing the various methods described herein to increase Lgr5+ cochlear cell proliferation. The cochlear cell is contacted with a FOXO inhibitor and optionall an HDAC inhibitor, as expressly described herein (collectively referred to herein as the "compound(s)") at a "cell effective concentration".

A cell effective concentration is the minimum concentration of the compound that induces at least an 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more in gene expression and/or about a 1.5-fold increase in number of Lgr5+ cells in a Stem Cell Proliferation Assay compared to a control.

In some embodiments, the Lgr5+ cochlear cell is contacted in vitro with the compound(s) at the "cell effective concentration", such as for example, in a cell culture (and then implanted into the cochlea). In other embodiments, the Lgr5+ cochlear cell is contacted with the compound(s) at the "cell effective concentration", in situ (i.e., within the cochlea). In some embodiments, sufficient compound is delivered the achieve the "cell effective concentration" throughout the speech region of the human cochlea. In order to achieve this target concentration, a higher concentration of drug may be instilled in the cochlea and diffuse throughout the speech region. In other embodiments, the Lgr5+ cochlear cell is contacted with the compound(s) at 2, 3, 4, 5, 10, 20, or 50-fold more than the "cell effective concentration", in situ (i.e., within the cochlea).

Alternatively, hearing loss or reduced auditory function is treated by administering the compound(s) at the "formulation effective concentration". A "formulation effective concentration" is a higher concentration than the "cell effective formulation". For example, the "formulation effective concentration" is at least about 100 to 5000 fold higher than the "cell effective concentration", or about 20 to 2000 fold higher than the "cell effective concentration", or about 100 to 1000 fold higher than the "cell effective concentration". Typically, the "formulation effective concentration" is at least about 1000 fold higher than the "cell effective concentration". In some embodiments, compound(s) at the "formulation effective concentration" are introduced into the middle ear. The compound(s) are formulated at the "formulation effective concentration" as described supra.

In some embodiments, the "cell effective concentration" is about 0.01 uM to 1000 mM, about 0.1 uM to 1000 mM, about 1 uM to 100 mM, about 10 uM to 10 mM, about 1 uM to 10 uM, about 10 uM to 100 uM, about 100 uM to 1000 uM, about 1 mM to 10 mM, or about 10 mM to 100 mM.

In some embodiments, the "formulation effective concentration" is about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM In some embodiments, the FOXO inhibitor is AS1842856 and the "cell effective concentration" is about 0.01 uM to 1000 mM, about 0.1 uM to 1000 mM, about 1 uM to 100 mM, about 10 uM to 10 mM, about 1 uM to 10 uM, about 10 uM to 100 uM, about 100 uM to 1000 uM, about 1 mM to 10 mM, or about 10 mM to 100 mM. Preferably, the AS1842856 "cell effective concentration" is about 0.1 uM, 0.2 uM, 0.3 uM, 0.4 uM, 0.5 uM, 0.6 uM, 0.7 uM, 0.8 uM, 0.9 uM, or 1 uM.

In some embodiments, the FOXO inhibitor is AS1842856 and the "formulation effective concentration" is about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM. Preferably, the AS1842856 "formulation effective concentration" is about 0.1 mM, 0.2 mM, 0.3 mM, 0.4 mM, 0.5 mM, 0.6 mM, 0.7 mM, 0.8 mM, 0.9 mM, or 1 mM.

In some embodiments, the pharmaceutical composition comprises an epigenetic agent that is an HDAC inhibitor at a concentration about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM.

In some embodiments, the pharmaceutical composition comprises a HDAC inhibitor that is VPA at a concentration about 100 mM to 4,000 mM.

In some embodiments, the pharmaceutical composition comprises VPA at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of VPA at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises a HDAC inhibitor that is is 2-hexyl-4-pentynoic acid at concentration about 100 mM to 4,000 mM.

In some embodiments, the pharmaceutical composition comprises 2-hexyl-4-pentynoic acid at a unit dose of 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of 2-hexyl-4-pentynoic acid at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises, Na phenylbutyrate that is at a concentration about 100 mM to 4,000 mM.

In some embodiments, the pharmaceutical composition comprises Na phenylbutyrate at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of the Na phenylbutyrate at a unit dose of about 50 mg, about 100 mg, about 125 mg, about 250 mg, about 500 mg, 1000 mg, 2000 mg, 3000 mg, 4000 mg, or about 5000 mg Some embodiments include combination therapies, which comprise contacting the cell or administering (i) the FOXO inhibitor in combination with a (ii) HDAC inhibitor, wherein the combination increases Lgr5+ cochlear cell proliferation relative to each of (i) and (ii) alone. In some instances, the combination is administered transtympanically to the subject. Some embodiments comprise administering the (i) FOXO inhgibitor and (ii) an HDAC inhibitor together in the same pharmaceutical composition, as described herein. Some embodiments comprise administering the (i) FOXO inhibitor and the (ii) the HDAC inhibitor separately in separate pharmaceutical compositions. In some embodiments, administering the combination of (i) and (ii) results in improved hearing in the subject relative to each of (i) and (ii) alone.

Exemplary combinations therapies include administering AS1842856 and VPA.

In some embodiments the combination therapy includes AS1842856 and VPA where AS1842856 is at a "cell effective concentration" of about between 0.010 uM to 10 uM and VPA is at a cell effective" concentration of about between 10 uM to 10,000 uM. Alternatively, AS1842856 is at a "formulation effective concentration" of about between 0.010 mM to 10 mM and VPA is a formulation effective" concentration of about between 10 mM to 10,000 mM.

Pharmaceutical Compositions and Administration

Certain embodiments relate to pharmaceutical, prophylactic, and/or therapeutic compositions, comprising a pharmaceutically-acceptable carrier and a PI3K a PI3K synergist, a pharmaceutically-acceptable salt thereof or combinations thereof as described herein (collectively referred to herein as the "compound(s)").

In some embodiments, the concentration of the compound(s) in the pharmaceutical compositions of the invention are at the "formulation effective concentration" as described supra.

In some embodiments, the pharmaceutical composition comprises a FOXO inhibitor that is AS1842856 at a concentration of about 10 uM to 1,000,000 mM, about 100 uM to 1,000,000 mM, about 1000 uM to 100,000 mM, about 10,000 uM to 10,000 mM, about 1,000 uM to 10,000 uM, about 10,000 uM to 100,000 uM, about 100,000 uM to 1,000,000 uM, about 1000 mM to 10,000 mM, or about 10,000 mM to 100,000 mM. Preferably, the AS1842856 "formulation effective concentration" is about 0.1 mM, 0.2 mM, 0.3 mM, 0.4 mM, 0.5 mM, 0.6 mM, 0.7 mM, 0.8 mM, 0.9 mM, or 1 mM.

In some embodiments, the pharmaceutical composition comprises an epigenetic agent that is an HDAC inhibitor at a concentration about 10 uM to 1,000,000 mM, about 1000 uM to 100,000 mM, about 10,000 uM to 10,000 mM, about 1000 uM to 10,000 uM, about 10,000 uM to 100,000 uM, about 100,000 uM to 1,000,000 uM, about 1,000 mM to 10,000 mM, or about 10,000 mM to 100,000 mM.

In some embodiments, the pharmaceutical composition comprises a HDAC inhibitor that is VPA at a concentration about 100 mM to 4,000 mM.

In some embodiments, the pharmaceutical composition comprises VPA at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of VPA at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises a HDAC inhibitor that is is 2-hexyl-4-pentynoic acid at concentration about 100 mM to 4,000 mM.

In some embodiments, the pharmaceutical composition comprises 2-hexyl-4-pentynoic acid at a unit dose of 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of 2-hexyl-4-pentynoic acid at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises, Na phenylbutyrate that is at a concentration about 100 mM to 4,000 mM.

In some embodiments, the pharmaceutical composition comprises Na phenylbutyrate at a unit dose of about 50 mg, about 100 mg, about 125 mg, about 250 mg, about 500 mg, 1000 mg, 2000 mg, 3000 mg, 4000 mg, or about 5000 mg In some embodiments, the pharmaceutical composition comprises an oral dosage form of the Na phenylbutyrate at a unit dose of about 50 mg, about 100 mg, about 125 mg, about 250 mg, about 500 mg, 1000 mg, 2000 mg, 3000 mg, 4000 mg, or about 5000 mg In some embodiments the pharmaceutical composition comprises AS1842856 and VPA where AS1842856 is at a concentration of about between 0.010 mM to 10 mM and VPA is at concentration of about between 100 mM to 4,000 mM.

In some embodiments the pharmaceutical composition comprises AS1842856 and VPA where AS1842856 is at a concentration of about between 0.010 mM to 10 mM and VPA is unit dose (e.g. an oral unit dose) of about 50 mg, about 100 mg, about 125 mg, about 250 mg, about 500 mg, 1000 mg, 2000 mg, 3000 mg, 4000 mg, or about 5000 mg In some embodiments, as noted above, a composition is adapted for administration to the inner ear and/or middle ear, for example, local administration to the round window membrane or intratympanic or transtympanic administration, for example, to cochlear tissue.

The phrase "pharmaceutically-acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically-acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically-acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

Certain compositions comprise at least one biocompatible matrix. The term "biocompatible matrix" as used herein is a polymeric carrier that is acceptable for administration to humans for the release of therapeutic agents. In some instances, a biocompatible matrix may be a biocompatible gel or foam.

Certain compositions comprise at least on poloxamer. Poloxamers are triblock copolymers formed of (i.e., hydrophilic poly(oxyethylene) blocks and hydrophobic poly(oxypropylene) blocks) configured as a triblock of poly(oxyethylene)-poly(oxypropylene)-poly(oxyethylene). Poloxamers are one class of block copolymer surfactants having a propylene oxide block hydrophobe and an ethylene oxide hydrophile. Poloxamers are commercially available (e.g., Pluronic® polyols are available from BASF Corporation). Alternatively, poloxamers can be synthesized by known techniques.

Exemplary poloxamers include Poloxamer 124, Poloxamer 188, Poloxamer 237, Poloxamer 338, and Poloxamer 407. In some embodiments, the poloxamer comprises mixtures of two or more of Poloxamer 124, Poloxamer 188, Poloxamer 237, Poloxamer 338 or Poloxamer 407. In some embodiments, the mixture of two or more poloxamers comprise Poloxamer 407 and Poloxamer 124. In certain embodiments the poloxamer comprises at least one of Poloxamer 188 and Poloxamer 407 or mixtures thereof. In some embodiments, the poloxamer is Poloxamer 407.

In some embodiments, the poloxamer is in a concentration between about 5 wt % and about 25 wt % relative to the composition, or about 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, 21 wt %, 22 wt %, 23 wt %, 24 wt %, or 25 wt % relative to the composition. In certain embodiments, the poloxamer is in a concentration between about 10 wt % and about 23 wt % relative to the composition. In some embodiments the poloxamer is in a concentration between about 15 wt % and about 20 wt % relative to the composition. In particular embodiments, the poloxamer is in a concentration is approximately 17 wt % relative to the composition.

In some embodiments, wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Certain compositions comprise at least one antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In specific embodiments, the viscosity of the composition at about body temperature is substantially different (e.g., lesser, greater) than the viscosity of the composition at room temperature.

In some embodiments, the composition comprises a buffer. For example, in certain instances, the buffer is physiological saline or phosphate-buffered saline (PBS).

In some embodiments, the composition is at or near physiological pH. For instance, in some embodiments, the composition has a pH of between about 6 and about 8, including all integers, decimals, and ranges in between, for example, about 6 to about 6.5 to about 7 to about 7.5 to about 8. In specific embodiments, the composition has a pH of about 7.4 (±0.2).

Compounds or compositions described herein can be formulated in any manner suitable for a desired delivery route, e.g., transtympanic injection, transtympanic wicks and catheters, cochlear implants, and injectable depots. In some instances, compositions or formulations include one or more physiologically-acceptable components, including derivatives or prodrugs, solvates, stereoisomers, racemates, or tautomers thereof with any physiologically acceptable carriers, diluents, and/or excipients.

As noted above, certain compositions are adapted for, and certain methods employ, administration to the middle ear or inner ear, for example, by local administration to the round window membrane. The membrane of the round window is the biological barrier to the inner ear space and represents the major obstacle for the local treatment of hearing impairment. The administered drug must overcome this membrane to reach the inner ear space. The drug can operatively (e.g., injection through the tympanic membrane) be placed locally to the round window membrane and can then penetrate through the round window membrane. Substances that penetrate the round window typically distribute in the perilymph and thus reach the hair cells and supporting cells.

The pharmaceutical compositions or formulations may also contain a membrane penetration enhancer, which supports the passage of the agents mentioned herein through the round window membrane. Accordingly, liquid, gel or foam formulations may be used. It is also possible to apply the active ingredient orally or to employ a combination of delivery approaches.

Certain compositions are adapted for, and certain methods employ, administration to the middle ear or inner ear, for example, by intratympanic or transtympanic administration. Intratympanic (IT) delivery of drugs to the ear is increasingly used for both clinical and research purposes. Some groups have applied drugs in a sustained manner using microcatheters and microwicks, while the majority have applied them as single or as repeated IT injections (up to 8 injections over periods of up to 2 weeks).

Intratympanically applied drugs are thought to enter the fluids of the inner ear primarily by crossing the round window (RW) membrane. Calculations show that a major factor controlling both the amount of drug entering the ear and the distribution of drug along the length of the ear is the duration the drug remains in the middle ear space. Single, 'one-shot' applications or applications of aqueous solutions for few hours' duration result in steep drug gradients for the applied substance along the length of the cochlea and rapidly declining concentration in the basal turn of the cochlea as the drug subsequently becomes distributed throughout the ear.

Other injection approaches include by osmotic pump, or, by combination with implanted biomaterial, and more preferably, by injection or infusion. Biomaterials that can aid in controlling release kinetics and distribution of drug include hydrogel materials, degradable materials. One class of materials that is most preferably used includes in situ gelling materials. All potential materials and methodologies mentioned in references (Almeida H, Amaral M H, Lobao P, Lobo J M, Drug Discov Today 2014; 19:400-12; Wise A K, Gillespie L N, J Neural Eng 2012; 9:065002; Surovtseva E V, Johnston A H, Zhang W, et al, Int J Pharmaceut 2012; 424:121-7; Roy S, Glueckert R, Johnston A H, et al., Nanomedicine 2012; 7:55-63; Rivera T, Sanz L, Camarero G, Varela-Nieto I., Curr Drug Deliv 2012; 9:231-42; Pararas E E, Borkholder D A, Borenstein J T, Adv Drug Deliv Rev 2012; 64:1650-60; Li M L, Lee L C, Cheng Y R, et al., IEEE T Bio-Med Eng 2013; 60:2450-60; Lajud S A, Han Z, Chi F L, et al., J Control Release 2013; 166:268-76; Kim D K, Park S N, Park K H, et al., Drug Deliv 2014; Engleder E, Honeder C, Klobasa J, Wirth M, Arnoldner C, Gabor F, Int J Pharmaceut 2014; 471:297-302; Bohl A, Rohm H W, Ceschi P, et al., J Mater Sci Mater Med 2012; 23:2151-62; Hoskison E, Daniel M, Al-Zahid S, Shakesheff K M, Bayston R, Birchall J P, Ther Deliv 2013; 4:115-24; Staecker H, Rodgers B, Expert Opin Drug Deliv 2013; 10:639-50; Pritz C O, Dudas J, Rask-Andersen H, Schrott-Fischer A, Glueckert R, Nanomedicine 2013; 8:1155-72), which are included herein by reference in their entirety. Other materials include collagen or other natural materials including fibrin, gelatin, and decellularized tissues. Gelfoam may also be suitable.

Delivery may also be enhanced via alternate means including but not limited to agents added to the delivered composition such as penetration enhancers, or could be through devices via ultrasound, electroporation, or high-speed jet.

Methods described herein can also be used for inner ear cell types that may be produced using a variety of methods know to those skilled in the art including those cell types described in PCT Application No. WO2012103012 A1.

With regard to human and veterinary treatment, the amount of a particular agent(s) that is administered may be dependent on a variety of factors, including the disorder being treated and the severity of the disorder; activity of the specific agent(s) employed; the age, body weight, general health, sex and diet of the patient; the time of administration, route of administration, and rate of excretion of the specific agent(s) employed; the duration of the treatment; drugs used in combination or coincidental with the specific agent(s) employed; the judgment of the prescribing physician or veterinarian; and like factors known in the medical and veterinary arts.

The agents described herein may be administered in a therapeutically effective amount to a subject in need of treatment. Administration of compositions (e.g., compositions comprising a PI3K agonist optionally in combination with a PI3K synergist or HDAC inhibitor described herein can be via any of suitable route of administration, for example, by intratympanic administration. Other routes include ingestion, or alternatively parenterally, for example intravenously, intra-arterially, intraperitoneally, intrathecally, intraventricularly, intraurethrally, intrasternally, intracranially, intramuscularly, intranasally, subcutaneously, sublingually, transdermally, or by inhalation or insufflations, or topical by ear instillation for absorption through the skin of the ear canal and membranes of the eardrum. Such administration may be as a single or multiple oral dose, defined number of ear drops, or a bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds are preferably formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives.

Compositions described herein can be administered by several methods sufficient to deliver the composition to the inner ear. Delivering a composition to the inner ear includes administering the composition to the middle ear, such that the composition may diffuse across the round window to the inner ear. It also includes administering a composition to the inner ear by direct injection through the round window membrane. Such methods include, but are not limited to auricular administration, by transtympanic wicks or catheters, or parenteral administration, for example, by intraauricular, transtympanic, or intracochlear injection.

In particular embodiments, the compounds, compositions and formulations of the disclosure are locally administered, meaning that they are not administered systemically.

In one embodiment, a syringe and needle apparatus is used to administer compounds or compositions to a subject using auricular administration. A suitably sized needle is used to pierce the tympanic membrane and a wick or catheter comprising the composition is inserted through the pierced tympanic membrane and into the middle ear of the subject. The device may be inserted such that it is in contact with the round window or immediately adjacent to the round window. Exemplary devices used for auricular administration include, but are not limited to, transtympanic wicks, transtympanic catheters, round window microcatheters (small catheters that deliver medicine to the round window), and Silverstein Microwicks™ (small tube with a "wick" through the tube to the round window, allowing regulation by subject or medical professional).

In some embodiments, a syringe and needle apparatus is used to administer compounds or compositions to a subject using transtympanic injection, injection behind the tympanic membrane into the middle and/or inner ear. The formulation may be administered directly onto the round window membrane via transtympanic injection or may be administered directly to the cochlea via intracochlear injection or directly to the vestibular organs via intravestibular injection.

In some embodiments, the delivery device is an apparatus designed for administration of compounds or compositions to the middle and/or inner ear. By way of example only: GYRUS Medical GmbH offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver compositions to the inner ear. U.S. Patent Application Publication 2007/0167918, which is incorporated herein by reference for such disclosure, further describes a combined otic aspirator and medication dispenser for transtympanic fluid sampling and medicament application.

In some embodiments, a compound or composition disclosed herein is administered to a subject in need thereof once. In some embodiments, a compound or composition disclosed herein is administered to a subject in need thereof more than once. In some embodiments, a first administration of a compound or composition disclosed herein is followed by a second, third, fourth, or fifth administration of a compound or composition disclosed herein.

The number of times a compound or composition is administered to an subject in need thereof depends on the discretion of a medical professional, the disorder, the severity of the disorder, and the subject's response to the formulation. In some embodiments, the compound or composition disclosed herein is administered once to a subject in need thereof with a mild acute condition. In some embodiments, a compound or composition disclosed herein is administered more than once to a subject in need thereof with a moderate or severe acute condition. In the case wherein the subject's condition does not improve, upon the doctor's discretion the compound or composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the compound or composition may administered continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once the subject's hearing and/or balance has improved, a maintenance dose can be administered, if necessary. Subsequently, the dosage or the frequency of administration, or both, is optionally reduced, as a function of the symptoms, to a level at which the improved disease, disorder or condition is retained. In certain embodiments, subjects require intermittent treatment on a long-term basis upon any recurrence of symptoms.

Definitions

In this application, the use of "or" includes "and/or" unless stated otherwise. As used in this application, the term "comprise" and variations of the term, such as "comprising"

and "comprises," are not intended to exclude other additives, components, integers or steps. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether they materially affect the activity or action of the listed elements.

The terms "about" and "approximately" are used as equivalents. Any numerals used in this disclosure with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Activity" refers to biological function mediated by proteins of a cell measured by methods known in the art such as immunostaining and western blotting in conjunction with cellular effects such as proliferation, cellular growth, or cellular gene expression.

"Administration" refers to introducing a substance into a subject. In some embodiments, administration is auricular, intraauricular, intracochlear, intravestibular, or transtympanically, e.g., by injection. In some embodiments, administration is directly to the inner ear, e.g. injection through the round window, otic capsule, or vestibular canals. In some embodiments, administration is directly into the inner ear via a cochlear implant delivery system.

In some embodiments, the substance is injected transtympanically to the middle ear. In certain embodiments "causing to be administered" refers to administration of a second component after a first component has already been administered (e.g., at a different time and/or by a different actor).

"Agonist" refers to an agent that causes an increase in the expression, levels, and/or activity of a target gene, protein, and/or pathway. In some instances, an agonist directly binds to and activates a target protein. In some instances, an agonist increases the activity of a pathway by binding to and modulating the activity of one or more pathway components, for example, by inhibiting the activity of negative regulator(s) of the pathway, or by activating upstream or downstream regulator(s) of the pathway.

An "antibody" refers to an immunoglobulin polypeptide, or fragment thereof, having immunogen binding ability.

"Antisense" refers to a nucleic acid sequence, regardless of length, that is complementary to the coding strand or mRNA of a nucleic acid sequence. Antisense RNA can be introduced to an individual cell, tissue or organoid. An anti-sense nucleic acid can contain a modified backbone, for example, phosphorothioate, phosphorodithioate, or other modified backbones known in the art, or may contain non-natural internucleoside linkages.

As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

"Auricular administration" refers to a method of using a catheter or wick device to administer a composition across the tympanic membrane to the inner ear of the subject. To facilitate insertion of the wick or catheter, the tympanic membrane may be pierced using a suitably sized syringe or pipette. The devices could also be inserted using any other methods known to those of skill in the art, e.g., surgical implantation of the device. In particular embodiments, the wick or catheter device may be a stand-alone device, meaning that it is inserted into the ear of the subject and then the composition is controllably released to the inner ear. In other particular embodiments, the wick or catheter device may be attached or coupled to a pump or other device that allows for the administration of additional compositions. The pump may be automatically programmed to deliver dosage units or may be controlled by the subject or medical professional.

"Cell Aggregate" as used herein refers to a body cells in the organ of Corti that have proliferated to form a cluster of a given cell type that is greater than 40 microns in diameter and/or produced a morphology in which greater than 3 cell layers reside perpendicular to the basilar membrane.

"Cell Aggregate" can also refer a process in which cell division creates a body of cells that cause one or more cell types to breach the reticular lamina, or the boundary between endolymph and perilymph.

"Cell Density" as used herein in connection with a specific cell type is the mean number of that cell type per area in a Representative Microscopy Sample. The cell types may include but are not limited to Lgr5+ cells, hair cells, or supporting cells. The Cell Density may be assessed with a given cell type in a given organ or tissue, including but not limited to the cochlea or organ of Corti. For instance, the Lgr5+ Cell Density in the organ of Corti is the Cell Density of Lgr5+ cells as measured across the organ of Corti. Typically, supporting cells and Lgr5+ cells will be enumerated by taking cross sections of the organ of Corti. Typically, hair cells will be enumerated by looking down at the surface of the organ of Corti, though cross sections may be used in some instances, as described in a Representative Microscopy Sample. Typically, Cell Density of Lgr5+ cells will be measured by analyzing whole mount preparations of the Organ of Corti and counting the number of Lgr5 cells across a given distance along the surface of the epithelia, as described in a Representative Microscopy Sample. Hair cells may be identified by their morphological features such as bundles or hair cell specific stains (e.g., Myosin VIIa, Prestin, vGlut3, Pou4f3, Espin, conjugated-Phalloidin, PMCA2, Ribeye, Atoh1, etc.). Lgr5+ cells may be identified by specific stains or antibodies (e.g., Lgr5-GFP transgenic reporter, anti-Lgr5 antibody, etc.)

"Cochlear Concentration" as used herein will be the concentration of a given agent as measured through sampling cochlear fluid or tissue. Unless otherwise noted, the sample should contain a substantial enough portion of the cochlear fluid or tissue so that it is approximately representative of the average concentration of the agent in the cochlea. For example, samples may be drawn from a vestibular canal, and a series of fluid samples drawn in series such that individual samples are comprised of cochlear fluid in specified portions of the cochlea "Complementary nucleic acid sequence" refers to a nucleic acid sequence capable of hybridizing with another nucleic acid sequence comprised of complementary nucleotide base pairs.

"Cross-Sectional Cell Density" as used herein in connection with a specific cell type is the mean number of that cell type per area of cross section through a tissue in a Representative Microscopy Sample. Cross sections of the organ of Corti can also be used to determine the number of cells in a given plane. Typically, hair cells Cross-sectional Cell Density will be measured by analyzing whole mount preparations of the organ of Corti and counting the number of hair cells across a given distance in cross sections taken along a portion of the epithelia, as described in a Representative Microscopy Sample. Typically, Cross-sectional Cell Density of Lgr5+ cells will be measured by analyzing whole mount preparations of the organ of Corti and counting the number of Lgr5+ cells across a given distance in cross sections taken along a portion of the epithelia, as described in a Representative Microscopy Sample. Hair cells may be identified by their morphological features such as bundles or hair cell specific stains (suitable stains include e.g., Myosin VIIa, Prestin, vGlut3, Pou4f3, conjugated-Phalloidin, PMCA2, Atoh1, etc.). Lgr5+ cells may be identified by specific stains or antibodies (suitable stains and antibodies include fluorescence in situ hybridization of Lgr5 mRNA, Lgr5-GFP transgenic reporter system, anti-Lgr5 antibodies, etc.).

"Decreasing" or "decreases" refers to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the level of reference or control.

"Decreasing" or "decreases" also includes decreasing by at least about 1.1-fold, for example, at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more, for example, as compared to the level of a reference or control.

"Effective Concentration" is the minimum concentration of a compound that induces at least an 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more in gene expression and/or about a 1.5-fold increase in number of Lgr5+ cells in a Stem Cell Proliferation Assay compared to the number of Lgr5+ cells in a Stem Cell Proliferation Assay performed without the compound.

"Effective Release Rate" (mass/time) as used herein is the Effective Concentration (mass/volume)*30 uL/1 hour.

"Eliminate" means to decrease to a level that is undetectable.

"Engraft" or "engraftment" refers to the process of stem or progenitor cell incorporation into a tissue of interest in vivo through contact with existing cells of the tissue. "Epithelial progenitor cell" refers to a multipotent cell which has the potential to become restricted to cell lineages resulting in epithelial cells.

"Epithelial stem cell" refers to a multipotent cell which has the potential to become committed to multiple cell lineages, including cell lineages resulting in epithelial cells.

"Expression" refers to gene levels as measured by the amount of RNA

"Fragment" refers to a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids of the reference nucleic acid molecule or polypeptide.

"HDAC inhibitor" refers to any compound that inhibits the cellular activity of Histone Deacetylase classes I-IV "Hybridize" refers to pairing to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507).

An "inhibitor" refers to an agent that causes a decrease in the expression, levels, and/or activity of a target gene, protein, and/or pathway. An "antagonist" is one example of an "inhibitor".

As used herein, an "inhibitory nucleic acid" is a double-stranded RNA, RNA interference, miRNA, siRNA, shRNA, or antisense molecule, or a portion thereof, or a mimetic thereof, that when administered to a mammalian cell results in a decrease in the expression of a target gene. Typically, a nucleic acid inhibitor comprises at least a portion of a target nucleic acid molecule, or an ortholog thereof, or comprises at least a portion of the complementary strand of a target nucleic acid molecule. In some instances, expression of a target gene is reduced by 10%, 25%, 50%, 75%, or even 90-100%.

"In Vitro Lgr5 activity" refers to the level of expression or activity of Lgr5 in an in vitro population of cells. It may be measured, for example, in cells derived from a Lgr5-GFP expressing mouse such as a B6.129P2-Lgr5tm1(cre/ERT2) Clea mouse (also known as Lgr5-EGFP-IRES-creERT2 or Lgr5-GFP mouse, Jackson Lab Stock No: 008875) by dissociating cells to single cells, staining with propidium iodide (PI), and analyzing the cells using a flow cytometer for Lgr5-GFP expression. Inner ear epithelial cells from wild-type (non-Lgr5-GFP) mice that passing the same culturing and analyzing procedures can be used as a negative control. Typically, two population of cells are shown in the bivariate plot with GFP/FITC as one variable, which include both GFP positive and GFP negative populations. Lgr5+ cells can be identified by gating GFP positive cell population. The percentage of Lgr5+ cells can be measured by gating GFP positive cell population against both GFP negative population and the negative control. The number of Lgr5+ cells can be calculated by multiplying the total number of cells by the percentage of Lgr5-positive cells. For cells derived from non-Lgr5-GFP mice, Lgr5 activity can be measured using an anti-Lgr5 antibody or quantitative-PCR on the Lgr5 gene.

"In Vivo Lgr5 activity" as used herein is the level of expression or activity of Lgr5 in a subject. It may be measured, for example, by removing an animal's inner ear and measuring Lgr5 protein or Lgr5 mRNA. Lgr5 protein production can be measured using an anti-Lgr5 antibody to measure fluorescence intensity as determined by imaging cochlear samples, where fluorescence intensity is used as a measure of Lgr5 presence. Western blots can be used with an anti-Lgr5 antibody, where cells can be harvested from the treated organ to determine increases in Lgr5 protein. Quantitative-PCR or RNA in situ hybridization can be used to measure relative changes in Lgr5 mRNA production, where cells can be harvested from the inner ear to determine changes in Lgr5 mRNA. Alternatively, Lgr5 expression can be measured using an Lgr5 promoter driven GFP reporter transgenic system, where the presence or intensity GFP fluoresce can be directly detected using flow cytometry, imaging, or indirectly using an anti-GFP antibody.

"Increasing" or "increases" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100, 150, 200, 250, 300, 350, 400, 450, or 500% or more, for example, as compared to the level of a reference.

"Increasing" or "increases" also means increases by at least about 1.1-fold, for example, at least about 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold or more, for example, as compared to the level of a reference standard.

"Intraauricular administration" refers to administration of a composition to the middle or inner ear of a subject by directly injecting the composition.

"Intracochlear" administration refers to direct injection of a composition across the tympanic membrane and across the round window membrane into the cochlea.

"Intravestibular" administration refers to direct injection of a composition across the tympanic membrane and across the round window or oval window membrane into the vestibular organs.

"Isolated" refers to a material that is free to varying degrees from components which normally accompany it as found in its native state. "Isolate" denotes a degree of separation from original source or surroundings.

"Lgr5" is an acronym for the Leucine-rich repeat-containing G-protein coupled receptor 5, also known as G-protein coupled receptor 49 (GPR49) or G-protein coupled receptor 67 (GPR67). It is a protein that in humans is encoded by the Lgr5 gene.

"Lgr5 Activity" is defined as the level of activity of Lgr5 in a population of cells. In an in vitro cell population, Lgr5 activity may be measured in an in vitro Lgr5 Activity assay. In an in vivo cell population, Lgr5 activity may be measured in an in vivo Lgr5 Activity assay.

"Lgr5+ cell" or "Lgr5-positive cell" as used herein is a cell that expresses Lgr5. "Lgr5-cell" or "Lgr5-negative" as used herein is a cell that is not Lgr5+.

"Lineage Tracing" as used herein is using a mouse line that enables fate tracing of any cell that expresses a target gene at the time of reporter induction. This can include hair cell or supporting cells genes (Sox2, Lgr5, MyosinVIIa, Pou4f3, etc.). For example, lineage tracing may use an Lgr5-EGFP-IRES-creERT2 mouse crossed with a reporter mouse, which upon induction, allows one to trace the fate of cells that expressed Lgr5 at the time of induction. By further example, Lgr5 cells can be isolated into single cells and cultured in a Stem Cell Proliferation Assay to generate colonies, then subsequently differentiated in a Differentiation Assay and analyzed for cell fate by staining for hair cell and/or supporting cell proteins and determining the reporter co-localization with either hair cell or supporting cell staining to determine the Lgr5 cells' fate. In addition, lineage tracing can be performed in cochlear explants to track supporting cell or hair cell fate within the intact organ after treatment. For example, Lgr5 cell fate can be determined by isolating the cochlea from a Lgr5-EGFP-IRES-creERT2 mouse crossed with a reporter mouse and inducing the reporter in Lgr5 cells before or during treatment. The organ can then be analyzed for cell fate by staining for hair cell and/or supporting cell proteins and determining the reporter co-localization with either hair cell or supporting cell staining to determine the Lgr5 cells' fate. In addition, lineage tracing can be performed in vivo track supporting cell or hair cell fate within the intact organ after treatment. For example, Lgr5 cell fate can be determined inducing a reporter in an Lgr5-EGFP-IRES-creERT2 mouse crossed with a reporter mouse, treating the animal, then isolating the cochlea. The organ can then be analyzed for cell fate by staining for hair cell and/or supporting cell proteins and determining the reporter co-localization with either hair cell or supporting cell staining to determine the Lgr5 cells' fate. Lineage tracing may be performed using alternative reporters of interest as is standard in the art.

"Mammal" refers to any mammal including but not limited to human, mouse, rat, sheep, monkey, goat, rabbit, hamster, horse, cow or pig.

"Mean Release Time" as used herein is the time in which one-half of an agent is released into phosphate buffered saline from a carrier in a Release Assay.

"Native Morphology" as used herein is means that tissue organization largely reflects the organization in a healthy tissue.

"Non-human mammal", as used herein, refers to any mammal that is not a human.

As used in relevant context herein, the term "number" of cells can be 0, 1, or more cells.

"Organ of Corti" as used herein refers to the sensory epithelia of the cochlea where the sensory cells (inner and outer hair cells) and supporting cells reside.

"Organoid" or "epithelial organoid" refers to a cell cluster or aggregate that resembles an organ, or part of an organ, and possesses cell types relevant to that particular organ.

"Pharmaceutically-acceptable salt" includes both acid and base addition salts.

"Pharmaceutically-acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Example organic bases used in certain embodiments include isopropylamine, diethylamine, ethanolamine, trimethylamine, dicyclohexylamine, choline, and caffeine.

"Population" of cells refers to any number of cells greater than 1, but is preferably at least 1×103 cells, at least 1×104 cells, at least at least 1×105 cells, at least 1×106 cells, at least 1×107 cells, at least 1×108 cells, at least 1×109 cells, or at least 1×1010 cells.

"Progenitor cell" as used herein refers to a cell that, like a stem cell, has the tendency to differentiate into a specific type of cell, but is already more specific than a stem cell and is pushed to differentiate into its "target" cell.

"Proliferation Period" as used herein is the duration of time in which tissue or cells are exposed to a PI3K Agonist alone or in combination with a PI3K Synergist.

In certain embodiments, the "purity" of any given agent or compound in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high performance liquid chromatography (HPLC), a well-known form of column chromatography used frequently in biochemistry and analytical chemistry to separate, identify, and quantify compounds.

"Reference" means a standard or control condition (e.g., untreated with a test agent or combination of test agents).

"Release Assay" as used herein is a test in which the rate of release of an agent from a Biocompatible Matrix through dialysis membrane to a saline environment. An exemplary Release Assay may be performed by placing 30 microliters of a composition in 1 ml Phosphate Buffered Saline inside saline dialysis bag with a suitable cutoff, and placing the dialysis bag within 10 mL of Phosphate Buffered Saline at 37° C. The dialysis membrane size may be chosen based on agent size in order to allow the agent being assessed to exit the membrane. For small molecule release, a 3.5-5 kDa cutoff may be used. The Release Rate for a composition may change over time and may be measured in 1 hour increments.

"Representative Microscopy Sample" as used herein describes a sufficient number of fields of view within a cell culture system, a portion of extracted tissue, or an entire extracted organ that the average feature size or number being measured can reasonably be said to represent the average feature size or number if all relevant fields were measured. For example, in order to assess the hair cell counts at a frequency range on the Organ of Corti, ImageJ software (NIH) can used to measure the total length of cochlear whole mounts and the length of individual counted segments. The total number of inner hair cells, outer hair cells, and supporting cells can be counted in the entire or fraction of any of the four cochlear segments of 1200-1400 μm (apical, mid-apical, mid-basal, and basal) at least 3 fields of view at 100 μm field size would be reasonably considered a Representative Microscopy Sample. A Representative Microscopy sample can include measurements within a field of view, which can be measured as cells per a given distance. A Representative Microscopy sample can be used to assess morphology, such as cell-cell contacts, cochlear architecture, and cellular components (e.g., bundles, synapses).

"Rosette Patterning" is a characteristic cell arrangement in the cochlea in which <5% hair cells are adjacent to other hair cells.

The term "sample" refers to a volume or mass obtained, provided, and/or subjected to analysis. In some embodiments, a sample is or comprises a tissue sample, cell sample, a fluid sample, and the like. In some embodiments, a sample is taken from (or is) a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

"Self-renewal" refers to the process by which a stem cell divides to generate one (asymmetric division) or two (symmetric division) daughter cells with development potentials that are indistinguishable from those of the mother cell. Self-renewal involves both proliferation and the maintenance of an undifferentiated state.

"siRNA" refers to a double stranded RNA. Optimally, an siRNA is 18, 19, 20, 21, 22, 23 or 24 nucleotides in length and has a 2 base overhang at its 3' end. These dsRNAs can be introduced to an individual cell or culture system. Such siRNAs are used to downregulate mRNA levels or promoter activity.

"Stem cell" refers to a multipotent cell having the capacity to self-renew and to differentiate into multiple cell lineages.

"Stem Cell Differentiation Assay" as used herein is an assay to determine the differentiation capacity of stem cells. In an exemplary Stem Cell Differentiation Assay, the number of cells for an initial cell population is harvested from a Atoh1-GFP mouse between the age of 3 to 7 days, by isolating the Organ of Corti sensory epithelium, dissociating the epithelium into single cells, and passing the cells through a 40 um cell strainer. Approximately 5000 cells are entrapped in 40 μl of culture substrate (for example: Matrigel (Corning, Growth Factor Reduced)) and placed at the center of wells in a 24-well plate with 500 μl of an appropriate culture media, growth factors and agent being tested. Appropriate culture media and growth factors include Advanced DMEM/F12 with media Supplements (1X N2, 1X B27, 2 mM Glutamax, 10 mM HEPES, 1 mM N-acetylcysteine, and 100 U/ml Penicillin/100 μg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% CO2, with media change every 2 days. These cells are then cultured by removing the Stem Cell Proliferation Assay agents and replacing with Basal culture media and molecules to drive differentiation. An appropriate Basal culture media is Advanced DMEM/F12 supplemented with 1X N2, 1X B27, 2 mM Glutamax, 10 mM HEPES, 1 mM N-acetylcysteine, and 100 U/ml Penicillin/100 μg/ml Streptomycin and appropriate molecules to drive differentiation are 3 μM CHIR99021 and 5 μM DAPT for 10 days, with media change every 2 days. The number of hair cells in a population may be measured by using flow cytometry for GFP. Hair cell differentiation level can further be assessed using qPCR to measure hair cell marker (e.g., Myo7a) expression level normalized using suitable and unregulated references or housekeeping genes (e.g., Hprt). Hair cell differentiation level can also be assessed by immunostaining for hair cell markers (e.g. Myosin7a, vGlut3, Espin, PMCAs, Ribeye, conjugated-phalloidin, Atohl, Pou4f3, etc.). Hair cell differentiation level can also be assessed by Western Blot for Myosin7a, vGlut3, Espin, PMCAs, Prestin, Ribeye, Atohl, Pou4f3.

"Stem Cell Assay" as used herein is an assay in which a cell or a cell population are tested for a series of criteria to determine whether the cell or cell population are stem cells or enriched in stem cells or stem cell markers. In a stem cell assay, the cell/cell population are tested for stem cell characteristics such as expression of Stem Cell Markers, and further optionally are tested for stem cell function, including the capacity of self-renewal and differentiation. Gene expression is measured using methods known in the art such as by PCR, Nanostring, immunostaining, RNAseq, RNA hybridization, or Western blot analysis.

"Stem Cell Proliferation Assay" as used herein is an assay to determine the capacity for agent(s) to induce the creation of stem cells from a starting cell population. In an exemplary Stem Cell Proliferation Assay, the number of cells for an initial cell population is harvested from a Lgr5-GFP mouse such as a B6.129P2-Lgr5tml(cre/ERT2)Cle/J mouse (also known as Lgr5-EGFP-IRES-creERT2 or Lgr5-GFP mouse, Jackson Lab Stock No: 008875) between the age of 0 to 5 days, by isolating the organ of Corti sensory epithelium and dissociating the epithelium into single cells. Approximately 5000 cells are entrapped in 40 µl of culture substrate (for example: Matrigel (Corning, Growth Factor Reduced)) and placed at the center of wells in a 24-well plate with 500 µl of an appropriate culture media, growth factors and agent being tested. Appropriate culture media and growth factors include Advanced DMEM/F12 with media Supplements (1X N2, 1X B27, 2 mM Glutamax, 10 mM HEPES, 1 mM N-acetylcysteine, and 100 U/ml Penicillin/100 µg/ml Streptomycin) and growth factors (50 ng/ml EGF, 50 ng/ml bFGF, and 50 ng/ml IGF-1) as well as the agent(s) being assessed are added into each well. Cells are cultured for 10 days in a standard cell culture incubator at 37° C. and 5% CO2, with media change every 2 days. The number of Lgr5+ cells is quantified by counting the number of cells identified as Lgr5+ in an In Vitro Lgr5 activity assay. The fraction of cells that are Lgr5+ is quantified by dividing the number of cells identified as Lgr5+ in a cell population by the total number of cells present in the cell population. The number of hair cells in a population may be measured by staining with hair cell marker (e.g., MyosinVIIa), or using an endogenous reporter of hair cell genes (e.g., Pou4f3-GFP, Atoh1-nGFP) and analyzing using flow cytometry. The fraction of cells that are hair cells is quantified by dividing the number of cells identified as hair cells in a cell population by the total number of cells present in the cell population. Gene and/or protein expression and/or activity is measured in this assay using methods known in the art such as by PCR, Nanostring, immunostaining, RNAseq, RNA hybridization, or Western blot analysis.

"Stem Cell Markers" as used herein can be defined as gene products (e.g. protein, RNA, etc.) that specifically expressed in stem cells. One type of stem cell marker is gene products that are directly and specifically support the maintenance of stem cell identity. Examples include Lgr5 and Sox2. Additional stem cell markers can be identified using assays that were described in the literatures. To determine whether a gene is required for maintenance of stem cell identity, gain-of-function and loss-of-function studies can be used. In gain-of-function studies, over expression of specific gene product (the stem cell marker) would help maintain the stem cell identity. While in loss-of-function studies, removal of the stem cell marker would cause loss of the stem cell identity or induced the differentiation of stem cells. Another type of stem cell marker is gene that only expressed in stem cells but does not necessary to have specific function to maintain the identity of stem cells. This type of markers can be identified by comparing the gene expression signature of sorted stem cells and non-stem cells by assays such as micro-array and qPCR. This type of stem cell marker can be found in the literature. (e.g. Liu Q. et al., Int J Biochem Cell Biol. 2015 March; 60:99-111. http://www.ncbi.nlm.nih.gov/pubmed/25582750). Potential stem cell markers include Ccdc121, Gdf10, Opcm1, Phex, etc. The expression of stem cell markers such as Lgr5 or Sox2 in a given cell or cell population can be measure using assays such as qPCR, immunohistochemistry, western blot, and RNA hybridization. The expression of stem cell markers can also be measured using transgenic cells express reporters which can indicate the expression of the given stem cell markers, e.g. Lgr5-GFP or Sox2-GFP. Flow cytometry analysis can then be used to measure the activity of reporter expression. Fluorescence microscopy can also be used to directly visualize the expression of reporters. The expression of stem cell markers may further be determined using microarray analysis for global gene expression profile analysis. The gene expression profile of a given cell population or purified cell population can be compared with the gene expression profile of the stem cell to determine similarity between the 2 cell populations. Stem cell function can be measured by colony forming assay or sphere forming assay, self-renewal assay and differentiation assay. In colony (or sphere) forming assay, when cultured in appropriate culture media, the stem cell should be able to form colonies, on cell culture surface (e.g. cell culture dish) or embedded in cell culture substrate (e.g. Matrigel) or be able to form spheres when cultured in suspension. In colony/sphere forming assay, single stem cells are seeded at low cell density in appropriate culture media and allowed to proliferate for a given period of time (7-10 days). Colony formed are then counted and scored for stem cell marker expression as an indicator of stemness of the original cell. Optionally, the colonies that formed are then picked and passaged to test its self-renewal and differentiation potential. In self-renewal assay, when cultured in appropriate culture media, the cells should maintain stem cell marker (e.g. Lgr5) expression over at least one (e.g., 1, 2, 3, 4, 5, 10, 20, etc.) cell divisions. In a Stem Cell Differentiation Assay, when cultured in appropriate differentiation media, the cells should be able to generate hair cell which can be identified by hair cell marker expression measured by qPCR, immunostaining, western blot, RNA hybridization or flow cytometry.

"Subject" includes humans and mammals (e.g., mice, rats, pigs, cats, dogs, and horses). In some embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Supporting Cell" as used herein in connection with a cochlear epithelium comprises epithelial cells within the organ of Corti that are not hair cells. This includes inner pillar cells, outer pillar cells, inner phalangeal cells, Deiter cells, Hensen cells, Boettcher cells, and/or Claudius cells.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" means nearly totally or completely, for instance, 95% or greater of some given quantity.

"Synergist" refers to a compound that causes a more than additive increase in target gene expression or protein levels by 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 500, 1000-fold more than the additive value of each compound used individually.

"Tissue" is an ensemble of similar cells from the same origin that together carry out a specific function including, for example, tissue of cochlear, such as the organ of Corti.

"Transtympanic" administration refers to direct injection of a composition across the tympanic membrane into the middle ear.

"Treating" as used herein in connection with a cell population means delivering a substance to the population to affect an outcome. In the case of in vitro populations, the substance may be directly (or even indirectly) delivered to the population. In the case of in vivo populations, the substance may be delivered by administration to the host subject.

"Vehicle Control" or "Control" refers to treatment with the carrier that is absent of drug, such as DMSO for in vitro assays, poloxamer for middle ear delivery, and/or carrier or solution used to deliver drug compounds to cochlear cells describe here.

EXAMPLES

Example 1

Materials and Methods

Mice for Cell Screening

Neonatal Lgr5-EGFP-IRES-Cre-ER mice (The Jackson Laboratory, strain 8875) were used to analyze the effects of small molecules on cochlear stem cell expansion (see Barker et al., Nature 449, 1003-7 (2007). This strain allowed for visualization and quantification of EGFP cells.

Cell Assays

All animal studies were conducted under an approved institutional protocol per National Institutes of Health guidelines. Using neonatal animals, cochleae were dissected and the organ of Corti (sensory epithelium) was separated from the stria vascularis (ion transport epithelium) and the modiolus (nerve tissue). Epithelia were then collected and treated with TrypLE for 15-20 minutes to obtain single cells. The cells were then filtered (40 mm) and suspended in a Matrigel (Corning) dome for 3D culture seeded at 0.5 cochlea per well.

Expansion of Lgr5 Cells: Cells were cultured in a 3D system and bathed in a serum free 1:1 mixture of DMEM and F12, supplemented with Glutamax (GIBCO), N2, B27 (Invitrogen), EGF (50 ng/mL; Chemicon), bFGF (50 ng/mL; Chemicon), IGF-1 (50 ng/mL; Chemicon), and small molecules for seven days. Media was changed every other day. Treatments were run in triplicate or quadruplicate.

Quantification of Cell Proliferation: Lgr5 cells were quantified after 7-10 days. Cell colonies were dissociated into single cells using TrypLE. The cells were then stained with propidium iodide (PI) and analyzed using a flow cytometer to count Lgr5-EGFP cells. The percentage of viable Lgr5 cells was plotted against the concentration in GraphPad Prism.

Example 2

FOXO1 Inhibition Enhances Expansion Of Cochlear Progenitor Cells

Figure 2A:
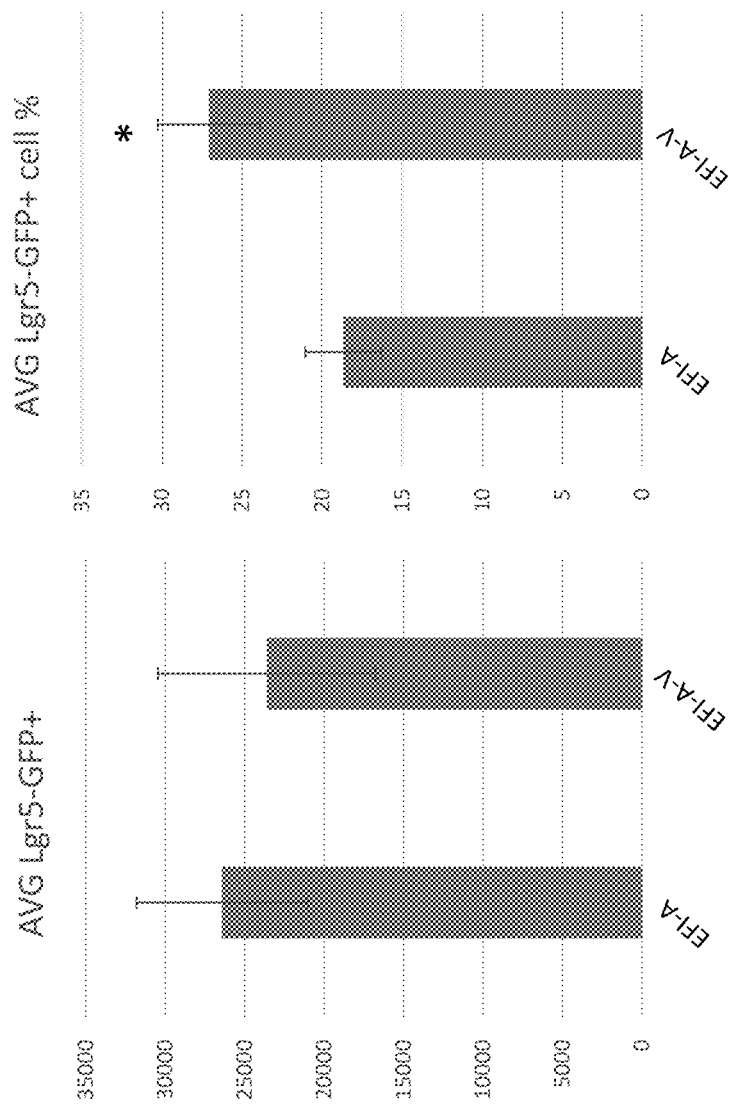
FIG. 2a displays that while in a background of EFI, AS1842856 (425 nM) elicits the expansion cochlear Lgr5+ progenitor cells in culture. Lgr5 cells are enriched according to percentage when AS1842856 is combined with VPA (1 mM).
Figure 2B:
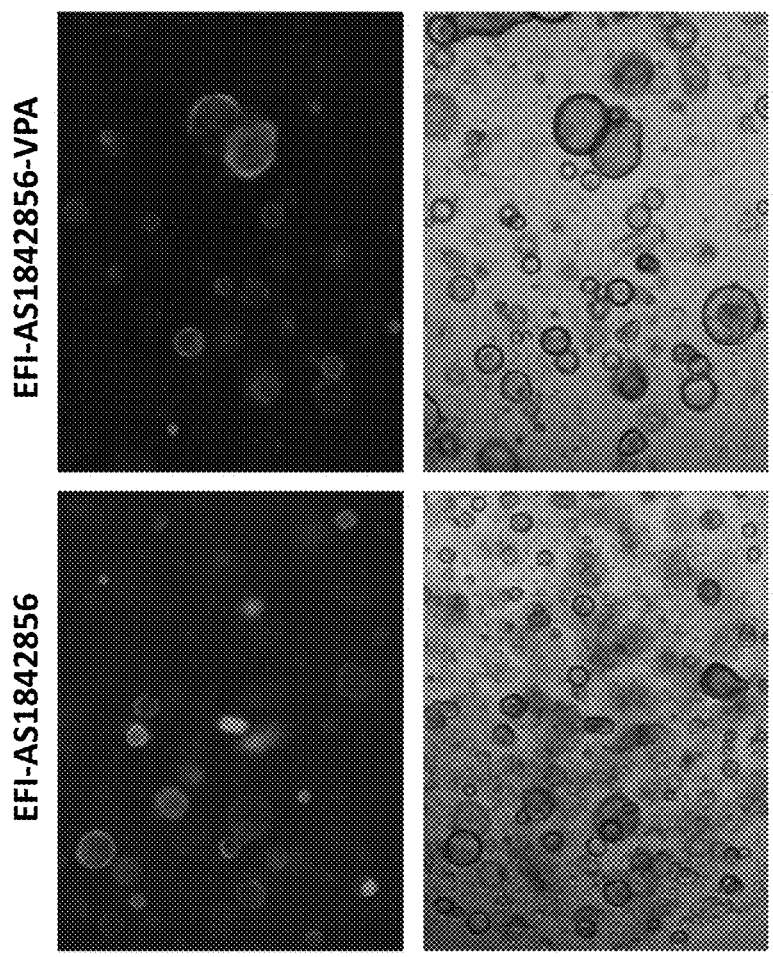
FIG. 2b. Images of Lgr5+ cell culture depicting Lgr5-GFP cell colonies. EFI-AS1842856 promotes Lgr5-GFP colony formation, which is enriched when VPA is added, as shown by less Lgr5-negative cells in culture.

As shown in FIG. 2, FOXO 1 inhibition with AS1842856 (EFI-A) enhances expansion of cochlear progenitor cells concentration-dependent manner. Moreover, as shown in FIGS. 2 A & B, Lgr5 cells are enriched when AS1842856 (425 nM) is combined with VPA (1 mM).

We claim:

1. A method for increasing proliferation of a cochlear supporting cell or a vestibular supporting cell, comprising contacting the cell with a composition comprising a Forkhead box-O transcription factor (FOXO) inhibitor, wherein the composition increases Lgr5+ cochlear cell proliferation compared to a vehicle control; wherein the composition is formulated for administration to the ear, the composition comprising a biocompatible matrix and one of:
   AS1842856;
   AS1842856 and valproic acid (VPA); or
   AS1842856 and a pharmaceutically acceptable salt of VPA.

2. A method of producing an expanded population of cochlear supporting cells or an expanded population of vestibular supporting cells, comprising contacting the population of cochlear supporting cells or vestibular supporting cells with a composition comprising a Forkhead box-O transcription factor (FOXO) inhibitor, thereby producing an expanded population of cochlear supporting cells or vestibular supporting cells, wherein the expanded population is capable of differentiating into hair cells as measured in a stem cell differentiation assay; wherein the composition is formulated for administration to the ear, the composition comprising a biocompatible matrix and one of:
   AS1842856;
   AS1842856 and valproic acid (VPA); or
   AS1842856 and a pharmaceutically acceptable salt of VPA.

3. A method of treating a subject who has, or is at risk of developing an inner ear hearing or balance disorder, comprising administering to the subject a composition; wherein the composition is formulated for administration to the ear, the composition comprising a biocompatible matrix and one of:
   AS1842856;
   AS1842856 and valproic acid (VPA); or
   AS1842856 and a pharmaceutically acceptable salt of VPA.

4. The method of claim 3, wherein the administration is to the tympanic membrane, the middle ear, or the inner ear.

5. A pharmaceutical composition formulated for administration to the ear, the composition comprising a biocompatible matrix and one of:
   AS1842856;
   AS1842856 and valproic acid (VPA); or
   AS1842856 and a pharmaceutically acceptable salt of VPA.

6. The pharmaceutical composition of claim 5, wherein the biocompatible matrix comprises hyaluronic acid, hyaluronate, lecithin gel, pluronic, poly(ethyleneglycol), poloxamer, chitosan, xyloglucan, collagen, fibrin, polyester, poly(lactide), poly(glycolide), poly(lactic-co-glycolic acid (PLGA), sucrose acetate isobutyrate, glycerol monooleate, poly anhydride, poly caprolactone sucrose, glycerol monooleate, silk material, or a combination thereof.

7. The pharmaceutical composition of claim 5, wherein the biocompatible matrix is a gel or a foam.

8. The pharmaceutical composition of claim 5, wherein the biocompatible matrix carrier comprises poloxamer.

9. The pharmaceutical composition of claim 8, wherein the poloxamer comprises at least one of Poloxamer 188, Poloxamer 407, or a mixture thereof.

10. The pharmaceutical composition of claim 8, wherein the poloxamer is at a concentration between about 5 wt % and about 25 wt %.

11. The pharmaceutical composition of claim 5, wherein AS1842856 is at a concentration of between about 10 μM to 1,000,000 mM.

12. The pharmaceutical composition of claim 5, wherein VPA is at a concentration of between about 10 mM and 10,000 mM.

13. The pharmaceutical composition of claim 5, wherein the composition is formulated for local administration to the round window membrane.

14. The pharmaceutical composition of claim 5, wherein the composition is formulated for transtympanic administration.

15. The pharmaceutical composition of claim 5, wherein the composition is formulated administration to the middle ear and/or inner ear.

* * * * *